United States Patent
Sugiyama et al.

(10) Patent No.: US 10,654,892 B2
(45) Date of Patent: May 19, 2020

(54) METHOD FOR ACTIVATING HELPER T CELL

(75) Inventors: Haruo Sugiyama, Osaka (JP); Shinji Sogo, Osaka (JP); Masayoshi Sato, Osaka (JP); Ryuki Kitamoto, Osaka (JP); Yoshihiro Goto, Osaka (JP)

(73) Assignees: International Institute of Cancer Immunology, Inc., Suita-shi (JP); OTSUKA PHARMACEUTICAL CO., LTD., Tokyo (JP)

( * ) Notice: Subject to any disclaimer, the term of this patent is extended or adjusted under 35 U.S.C. 154(b) by 957 days.

(21) Appl. No.: 13/877,768

(22) PCT Filed: Oct. 4, 2011

(86) PCT No.: PCT/JP2011/072874
§ 371 (c)(1),
(2), (4) Date: Jun. 21, 2013

(87) PCT Pub. No.: WO2012/046730
PCT Pub. Date: Apr. 12, 2012

(65) Prior Publication Data
US 2013/0266958 A1  Oct. 10, 2013

(30) Foreign Application Priority Data
Oct. 5, 2010 (JP) .................. 2010-225806

(51) Int. Cl.
*A61K 39/00* (2006.01)
*C12N 5/0783* (2010.01)
*C07K 7/08* (2006.01)
*C07K 14/82* (2006.01)
*A61K 35/17* (2015.01)

(52) U.S. Cl.
CPC ............ *C07K 7/08* (2013.01); *A61K 39/0011* (2013.01); *C07K 14/82* (2013.01); *C12N 5/0636* (2013.01); *C12N 5/0638* (2013.01); *A61K 35/17* (2013.01); *A61K 2039/5158* (2013.01); *A61K 2039/57* (2013.01); *C12N 2501/2302* (2013.01); *C12N 2501/2307* (2013.01)

(58) Field of Classification Search
None
See application file for complete search history.

(56) References Cited

U.S. PATENT DOCUMENTS

| | | |
|---|---|---|
| 7,030,212 B1 | 4/2006 | Sugiyama et al. |
| 7,063,854 B1 | 6/2006 | Gaiger et al. |
| 7,342,092 B2 | 3/2008 | Sugiyama |
| 7,378,384 B2 | 5/2008 | Sugiyama et al. |
| 7,390,871 B2 | 6/2008 | Sugiyama et al. |
| 7,420,034 B2 | 9/2008 | Sugiyama et al. |
| 7,517,950 B2 | 4/2009 | Sugiyama et al. |
| 7,608,685 B1 | 10/2009 | Sugiyama et al. |
| 7,622,119 B2 | 11/2009 | Sugiyama |
| 7,666,985 B2 | 2/2010 | Sugiyama et al. |
| 7,939,627 B2 | 5/2011 | Nishihara et al. |
| 8,105,604 B2 | 1/2012 | Sugiyama |
| 8,388,975 B2 | 3/2013 | Sugiyama |
| 8,765,687 B2 | 7/2014 | Scheinberg et al. |
| 9,233,149 B2 | 1/2016 | Scheinberg et al. |
| 2002/0128196 A1 | 9/2002 | Call et al. |
| 2004/0097703 A1 | 5/2004 | Sugiyama |
| 2004/0247609 A1 | 12/2004 | Sugiyama |
| 2005/0002951 A1 | 1/2005 | Sugiyama et al. |
| 2006/0121046 A1 | 6/2006 | Gaiger et al. |
| 2006/0165708 A1 | 7/2006 | Mayumi et al. |
| 2006/0217297 A1 | 9/2006 | Sugiyama et al. |
| 2007/0082860 A1 | 4/2007 | Sugiyama et al. |
| 2007/0128207 A1 | 6/2007 | Sugiyama |
| 2008/0070835 A1 | 3/2008 | Sugiyama |
| 2008/0152631 A1 | 6/2008 | Sugiyama |
| 2009/0099090 A1 | 4/2009 | Sugiyama et al. |
| 2009/0143291 A1 | 6/2009 | Sugiyama et al. |
| 2009/0263409 A1 | 10/2009 | Sugiyama |
| 2009/0281043 A1 | 11/2009 | Sugiyama et al. |
| 2010/0062013 A1 | 3/2010 | Sugiyama |

(Continued)

FOREIGN PATENT DOCUMENTS

| | | |
|---|---|---|
| CN | 1671733 A | 9/2005 |
| EP | 1 696 027 A1 | 8/2006 |

(Continued)

OTHER PUBLICATIONS

Karin et al (J. Exp. Med., 1994, 180: 2227-2237) (Year: 1994).*
Patel et al (PNAS, 1997, 94: 8082-8087) (Year: 1997).*
DiBrino et al (J. Immunology 151(11) 5930-5935, 1993) (Year: 1993).*
Celis et al (Molec. Immunol. 1994, 31(18): 1423-1430) (Year: 1994).*
Lin et al (J. Immunotherapy, 2013, 36: 159-170) (Year: 2013).*
Cancer.Net (2018) (Year: 2018).*
Sanmamed et al (Sem. Oncol. 2015, 42(4): 640-655) (Year: 2015).*
Office Action dated Sep. 8, 2014 in co-pending U.S. Appl. No. 12/449,765.

(Continued)

*Primary Examiner* — G. R. Ewoldt
*Assistant Examiner* — Marianne DiBrino
(74) *Attorney, Agent, or Firm* — Oblon, McClelland, Maier & Neustadt, L.L.P.

(57) ABSTRACT

The present invention relates to a method for activating helper T cells, which includes the step of activating helper T cells by adding a WT1 peptide to antigen presenting cells, wherein the WT1 peptide has the ability to bind to any MHC class II molecule of an HLA-DRB1*0101 molecule, an HLA-DRB1*0401 molecule, an HLA-DRB1*0403 molecule, an HLA-DRB1*0406 molecule, an HLA-DRB1*0803 molecule, an HLA-DRB1*0901 molecule, an HLA-DRB1*1101 molecule, an HLA-DRB3*0202 molecule, an HLA-DRB4*0101 molecule, an HLA-DPB1*0201 molecule or an HLA-DPB1*0301 molecule, and the like.

20 Claims, 9 Drawing Sheets
Specification includes a Sequence Listing.

(56) References Cited

U.S. PATENT DOCUMENTS

| | | |
|---|---|---|
| 2010/0092522 A1 | 4/2010 | Scheinberg et al. |
| 2010/0190163 A1 | 7/2010 | Sugiyama |
| 2010/0247556 A1 | 9/2010 | Sugiyama |
| 2010/0292160 A1 | 11/2010 | Sugiyama |
| 2011/0098233 A1 | 4/2011 | Sugiyama |
| 2012/0045465 A1 | 2/2012 | Sugiyama |
| 2012/0195918 A1 | 8/2012 | Sugiyama |
| 2013/0196427 A1 | 8/2013 | Sugiyama |
| 2013/0243800 A1 | 9/2013 | Sugiyama |
| 2015/0328278 A1 | 11/2015 | Kubo et al. |

FOREIGN PATENT DOCUMENTS

| | | |
|---|---|---|
| EP | 2 098 595 A1 | 9/2009 |
| JP | 2002-525099 A | 8/2002 |
| JP | 2006-280324 A | 10/2006 |
| WO | WO 00/18795 A2 | 4/2000 |
| WO | WO 01/62920 A2 | 8/2001 |
| WO | WO 02/099084 A2 | 12/2002 |
| WO | WO 03/002142 A1 | 1/2003 |
| WO | WO 03/028758 A1 | 4/2003 |
| WO | WO 03/106682 A1 | 12/2003 |
| WO | WO 2005/045027 A1 | 5/2005 |
| WO | WO 2005/095598 A1 | 10/2005 |
| WO | WO 2007/097358 A1 | 8/2007 |
| WO | WO 2008/081701 A1 | 7/2008 |
| WO | WO 2008/105462 A1 | 9/2008 |
| WO | WO 2010/123065 A1 | 10/2010 |

OTHER PUBLICATIONS

Office Action dated Apr. 3, 2012 in co-pending U.S. Appl. No. 12/449,765.
Office Action dated Mar. 17, 2015 in co-pending U.S. Appl. No. 12/449,765.
Office Action dated Sep. 26, 2012 in co-pending U.S. Appl. No. 12/449,765.
Office Action dated Sep. 7, 2015 in Chinese Patent Application No. 201310058504.4 (with English language translation).
Office Action dated May 14, 2014 in Canadian Patent Application No. 2,677,075.
Office Action dated Jul. 31, 2014 in Chinese Patent Application No. 201310009095.9 (with English language translation).
Office Action dated Jun. 23, 2015 in European Patent Application No. 11 830 662.0.
International Search Report dated May 13, 2008 in PCT/JP2008/053417 (with English language translation).
International Preliminary Report on Patentability and Written Opinion dated Sep. 1, 2009 in PCT/JP2008/053417 filed Feb. 27, 2008 (with English language translation).
International Search Report dated Feb. 25, 2014 in PCT/JP2013/083580 (submitting English translation only).
International Preliminary Report on Patentability and Written Opinion dated Jul. 2, 2015 in PCT/JP2013/083580 filed Dec. 16, 2013 (submitting English translation only).
Reexamination Decision dated Feb. 17, 2015 in Chinese Patent Application No. 200880006096.5 (with English language translation).
Office Action dated Oct. 23, 2014 in European Patent Application No. 08712039.0.
Combined Chinese Office Action and Search report dated Jun. 26, 2014 in Patent Application No. 201310058504.4 (with English language translation).
Office Action dated Dec. 12, 2013 in Indian Patent Application No. 4956/CHENP/2009.
Combined Chinese Office Action and Search Report dated Nov. 29, 2013 in Patent Application No. 201310009095.9 (with English language translation).
Office Action dated Aug. 14, 2013 in Russian Patent Application No. 2009135802/10 (with English language translation).
Office Action dated May 28, 2013 in Vietnamese Patent Application No. 1-2009-01834 (with English language translation).
Office Action dated May 28, 2013 in Colombian Patent Application No. 09-103858 (with partial English translation).
Office Action dated Dec. 31, 2012 in Malaysian Patent Application No. PI 20093253.
Office Action dated Dec. 12, 2012 in Russian Patent Application No. 2009135802/10 (with English language translation).
Office Action dated Oct. 2, 2012 in Australian Patent Application No. 2008220031.
Office Action dated Sep. 25, 2012 in Japanese Patent Application No. 2009-501276 (with partial English translation).
Office Action dated Aug. 22, 2012 in Colombian Patent Application No. 09-103858 (submitting English translation only).
Office Action dated Jun. 15, 2012 in Russian Patent Application No. 2009135802/10 (with English language translation).
Summary of Office Action dated Jun. 21, 2012 in Mexican Patent Application No. MX/a/2009/009168 (submitting English translation only).
Office Action dated Mar. 28, 2012 in Chinese Patent Application No. 200880006096.5 (with English language translation).
Extended European Search Report dated Jul. 20, 2010 in Patent Application No. 08712039.0.
Office Action dated May 5, 2011 in Chinese Patent Application No. 200880006096.5 (with English language translation).
Examination Report dated Sep. 23, 2011 in New Zealand Patent Application No. 578721.
Office Action dated Aug. 21, 2011 in Israeli Patent Application No. 200,161 (with partial English translation).
Office Action dated Nov. 8, 2011 in Chinese Patent Application No. 200880006096.5 (with English language translation).
Office Action dated Dec. 12, 2011 in Russian Patent Application No. 2009135802/10 (submitting English translation only).
Office Action dated Nov. 29, 2011 in Ukrainian Patent Application No. 200909812 (with English language translation).
Examination Report dated Jan. 9, 2012 in New Zealand Patent Application No. 578721.
Summary of Office Action dated Feb. 24, 2012 in Mexican Patent Application No. MX/a/2009/009168 (submitting English translation only).
Office Action dated Feb. 24, 2012 in European Patent Application No. 08 712 039.0.
Office Action dated Mar. 2, 2012 in Ukrainian Patent Application No. 200909812 (with English language translation).
"Do T-cells express MHC molecules?" Biology Stack Exchange, biology.stackexchange.com/questions/5612/do-t-cells-express-mhc-molecules, 2014, 1 Page.
R. Ian Freshney "Culture of Animal Cells: A Manual of Basic Technique" Alan R. Liss, Inc., 1983, 4 Pages.
Gerald B. Dermer "The Last Word: Another Anniversary for the War on Cancer" Bio/Technology, vol. 12, Mar. 1994, p. 320.
Marie Marchand, et al., "Biological and Clinical Developments in Melanoma Vaccines" Expert Opinion on Biological Therapy, vol. 1, No. 3, Ashley Publications Ltd. 1471-2598, 2001, pp. 497-510.
Philippe Fournier, et al., "Randomized clinical studies of anti-tumor vaccination: State of the art in 2008" Expert Reviews Vaccines, vol. 8, No. 1, 2009, pp. 51-66.
Taylor H. Schrieber, et al., "Tumor immunogenicity and responsiveness to cancer vaccine therapy: the state of the art" Seminars in Immunology, vol. 22, 2010, pp. 105-112.
Christopher A. Klebanoff, et al., "Therapeutic Cancer Vaccines: Are We There Yet?" Immunological Reviews, vol. 239, 2011, pp. 27-44.
Fumihiro Fujiki, et al., "Identification and Characterization of a WT1 (Wilms Tumor Gene) Protein-derived HLA-DRBI *0405-restricted 16-mer Helper Peptide That Promotes the Induction and Activation of WT1-specific Cytotoxic T Lymphocytes" Journal of Immunotherapy, vol. 30 No. 3, Apr. 2007, pp. 282-293.
Marie Marchand, et al., "Tumor regressions observed in patients with metastatic melanoma treated with an antigenic peptide encoded by gene MAGE-3 and presented by HLA-A1" International Journal of Cancer, vol. 80, No. 2, Jan. 1999, pp. 219-230.

(56) References Cited

OTHER PUBLICATIONS

Bela Bodey, et al., "Failure of Cancer Vaccines: The Significant Limitations of this Approach to Immunotherapy" Anticancer Research, vol. 20, 2000, pp. 2665-2676.
Ping Gao, et al., "Tumor Vaccination That Enhances Antitumor T-Cell Responses Does Not Inhibit the Growth of Established Tumors Even in Combination With Interleukin-12 Treatment: The Importance of Inducing Intratumoral T-Cell Migration" Journal of Immunotherapy, vol. 23, No. 6, http://ovidsp.tx.ovid.com/spa/ovidweb.cgi, 2000, pp. 643-653.
Esteban Celis "Getting Peptide Vaccines to Work: Just a Matter of Quality Control?" Journal of Clinical Investigation, vol. 110, No. 12, Dec. 15, 2002, pp. 1765-1768.
A_GENSEQ AEA15677, Jul. 28, 2005, 3 Pages.
Maresa Altomonte, et al., "Targeted therapy of solid malignancies via HLA class II antigens; a new biotherapeutic approach?" Oncogene, vol. 22, 2003, pp. 6564-6569.
Marlene Silva Bardi, et al., "HLA-A, B and DRB1 allele and haplotype frequencies in volunteer bone marrow donors from the north of Parana State" Revista Brasileira de Hematologia e Hemoterapia, vol. 34, No. 1, 2012, pp. 25-30.
Jörn Dengjel, et al., "Unexpected Abundance of HLA Class II Presented Peptides in Primary Renal Cell Carci nomas" Clinical Cancer Research, vol. 12, No. 14, Jul. 15, 2006, pp. 4163-4170 and Cover Page.
Fumihiro Fujiki, et al., "Identification of HLA-class II restricted WT1 peptide which can induce WT1-specific CD4+ helper T cells" Abstract 2-G-W29-08-O/P, Proceedings of the Japanese Society for Immunology, vol. 34, 2004, p. 210 and Cover Page (with English language translation).
Fumihiro Fujiki, et al. "Identification of WT1 peptide which can induce WT1-specific CD4+ helper T cells in an HLA-class II-restricted manner and examination of the usefulness of the peptide" Abstract 2-F-W27-8-O/P, Proceedings of the Japanese Society for Immunology, vol. 35, 2005, p. 187 and Cover Page (with English language translation).
Fang Han, et al., "HLA-DQ association and allele competition in Chinese narcolepsy" Tissue Antigens, vol. 80, 2012, pp. 328-335.
Peter Wendelboe Hansen, et al., "Cytotoxic Human HLA Class II Restricted Purified Protein Derivative-Reactive T-Lymphocyte Clones: IV. Analysis of HLA Restriction Pattern and Mycobacterial Antigen Specificity" Scandinavian Journal of Immunology, vol. 25, No. 3, 1987, pp. 295-303 and Cover Page.
Kimberley D. House, et al., "The search for a missing HLA-DRB1*09 Allele" Abstract 23-OR, 38th Annual Meeting of the American Society for Histocompatibility and Immunogenetics, Abstracts/Human Immunology, vol. 73, Oct. 8-12, 2012, p. 20 and Cover Pages.
Atsushi Irie, et al., "Establishment of HLA-DR4 transgenic mice having antigen-presenting function to HLA-DR4-restricted CD4+ Th cell" Abstract O-36(P-80), MHC (Major Histocompatibility Complex), Official Journal of the Japanese Society for Histocompatibility and Immunogenetics, vol. 19, No. 2, Aug. 10, 2012, p. 94 and Cover Pages (with English language translation).
Akiko Katsuhara, et al., "Transduction of a Novel HLA-DRB1*04:05-restricted, WT1-specific TCR Gene into Human CD4+ T Cells Confers Killing Activity Against Human Leukemia Cells" Anticancer Research, vol. 35, 2015, pp. 1251-1261.
Keith L. Knutson, et al., "Tumor antigen-specific T helper cells in cancer immunity and immunotherapy" Cancer Immunology, Immunotherapy, vol. 54, No. 8, 2005, pp. 721-728.
Yuhung Lin, et al., "HLA-DPB1*05:01-restricted WT1$_{332}$-specific TCR-transduced CD4+ T Lymphocytes Display a Helper Activity for WT1-specific CTL Induction and a Cytotoxicity Against Leukemia Cells" Journal of Immunotherapy, vol. 36, No. 3, Apr. 2013, pp. 159-170.
Peter S. Master, et al., "Patterns of Membrane Antigen Expression by AML Blasts: Quantitation and Histogram Analysis" Leukemia and Lymphoma, vol. 5, 1991, pp. 317-325.

Francesca Megiorni, et al., "HLA-DQA1 and HLA-DQB1 in Celiac disease predisposition: practical implications of the HLA molecular typing" Journal of Biomedical Science, vol. 19, No. 88, 2012, 5 pages.
A. S. Mustafa, et al., "BCG induced CD4+ cytotoxic T cells from BCG vaccinated healthy subjects: relation between cytotoxicity and suppression in vitro" Clinical and Experimental Immunology, vol. 69, No. 2, 1987, pp. 255-262.
Katayoun Rezvani, et al., "T-Cell Responses Directed against Multiple HLA-A*0201-Restricted Epitopes Derived from Wilms' Tumor 1 Protein in Patients with Leukemia and Healthy Donors: Identification, Quantification, and Characterization" Clinical Cancer Research, vol. 11, No. 24, Dec. 15, 2005, pp. 8799-8807 and Cover Page.
Shinji Sogo, "Final Study Report: Effect of OVT-101 on the Helper-activity Against WT1-specific CTL From Human Peripheral Blood Mononuclear Cells" Otsuka Pharmaceutical Co. Ltd., Study No. 030697, Report No. 025539, completed on Dec. 9, 2010 (22 pages).
Shinji Sogo, "Final Study Report: Cytolytic Activity of OCV-501-Specific Th1 Clones" Otsuka Pharmaceutical Co. Ltd., Study No. 035171, Report No. 028745, completed on Mar. 15, 2013 (39 pages).
Haruo Sugiyama, "WT1-targeting cancer vaccine" Japanese Journal of Clinical Medicine, vol. 70, No. 12, 2012, pp. 2105-2113 (Japanese with English abstract).
Haruo Sugiyama, "WT1 Peptide-Based Cancer Immunotherapy" Biotherapy, vol. 21, No. 5, Sep. 2007, pp. 299-306 (Japanese with English abstract).
K. L. Yang, et al., "An HLA-A*02:01-B*13:01-DRB1*14:01:03 haplotype conserved in Taiwanese and a possible close relationship between DRB1*14:01:03 and DRB1*14:54" International Journal of Immunogenetics, vol. 38, 2010, pp. 69-71.
Takuya Yazawa, et al., "Lack of class II transactivator causes severe deficiency of HLA-DR expression in small cell lung cancer" Journal of Pathology, vol. 187, 1999, pp. 191-199.
Steven G. E. Marsh, et al., "The HLA Facts Book," Academic Press, 2000, pp. 299, 377, and Cover Pages.
Sachiko Futami, et al., "HLA-DRB1*1502 Allele, Subtype of DR15, Is Associated with Susceptibility to Ulcerative Colitis and Its Progression" Digestive Diseases and Sciences, vol. 40, No. 4, Apr. 1995, pp. 814-818.
R. Sotiriadou, et al., "Peptide HER2(776-788) represents a naturally processed broad MHC class II-restricted T cell epitope" . British Journal of Cancer, vol. 85, No. 10, 2001, pp. 1527-1534.
John A. Hural, et al., "Identification of Naturally Processed CD4 T Cell Epitopes from the Prostate-Specific Antigen Kallikrein 4 Using Peptide-Based in Vitro Stimulation" The Journal of Immunology, vol. 169, No. 1, 2002, pp. 557-565 and Cover Page.
Office Action dated Jan. 19, 2016 in Canadian Patent Application No. 2,544,214.
Office Action dated Mar. 12, 2014 in Canadian Patent Application No. 2,544,214.
Office Action dated Mar. 7, 2014 in co-pending U.S. Appl. No. 13/755,185.
Office Action dated May 3, 2012 in Canadian Patent Application No. 2,544,214.
Office Action dated Jul. 27, 2010, in Japanese Patent Application No. 2005-515303.
Healthline.com; Non-hodgkin's Lymphoma in Depth—Overview: Learning Center on Healthline.com, healthline.com/channel/non -hodgkins-l ymphoma_indepth -overview, retrieved on Dec. 2, 2008.
Peter G. Maslak, et al., "Vaccination with synthetic analog peptides derived from WT1 oncoprotein induces T-cell responses in patients with complete remission from acute myeloid leukemia" , Clinical Trials and Observations, Blood, www.bloodjournal.org, vol. 116, No. 2, Jul. 15, 2010, pp. 171-179.
Akihiro Tsuboi, et al., "Enhanced induction of human WT1-specific cytotoxic T lymphocytes with a 9-mer WT1 peptide modified at HLA-A*2402-binding residues", Cancer Immunol Immunother, vol. 51, 2002, pp. 614-620.

(56) References Cited

OTHER PUBLICATIONS

Akiko Katsuhara, et al., "Transduction of a Novel HLA-DRB1*04:05-restricted, WT1-specific TCR Gene into Human CD4+ T Cells Confers Killing Activity Against Human Leukemia Cells", Anticancer Research, vol. 35, 2015, pp. 1251-1262.

Junji Yatsuda, et al., "Establishment of HLA-DR4 Transgenic Mice for the Identification of CD4+ T Cell Epitopes of Tumor-Associated Antigens", PLOS ONE, plosone.org, vol. 8, Issue No. 12, Dec. 2013, pp. 1-12.

Charles A. Janeway, Jr., et al., Immuno Biology, 5th edition, New York: Garland Science; 2001 ISBN-10: 0-8153-3642-X, Chapter 3, AW "The Immune System in Health and Disease", "Antigen Recognition by B-Cell and T-Cell Receptors", 7 pp., 2001.

Harpreet Singh et al., "Propred: Prediction of HLA-DR Binding Sites", Bioinformatics Centre, Institute of Microbial Technology, Sector 39A, Chandigarh-160036, India, Bioinformatics Applications Note, vol. 17, No. 12, 2001, pp. 1236-1237.

Wendy Bruening, et al., "Germline intronic and exonic mutations in the Wilms' tumour gene (WT1) affecting urogenital development" Nature Genetics, vol. 1, May 1992, pp. 144-148 (with GenBank: AAC60604.1).

Call, KM et al., "Antibodies Specific for Wilms' Tumor (WT) Protein Variant WT33, Useful in Immunoassays to Detect WT33 in Samples and Diagnose e.g. Sporadic Wilms' Tumors", cited in European Search Report of EP 09003839.9, AAG78443 standard; protein; 345 AA, WT33 Wilms' Tumour Protein, Database Geneseq, XP-002525443, dated Apr. 12, 2002, 2 pages.

Penn S.G., et al., "Human Genome-Derived Single Exon Nucleic Acid Probes Useful for Analyzing Gene Expression in Human Adult Liver", cited in European Search Report of EP 09003839.9, ABG52313 standard; peptide; 37 AA, Database Geneseq, Human Liver Peptide, SEQ ID No. 30961, XP-002525442, dated Feb. 25, 2003, 1 page.

Call, KM et al., "Antibodies Specific for Wilms' Tumor (WT) Protein Variant WT33, Useful in Immunoassays to Detect WT33 in Samples and Diagnose e.g. Sporadic Wilms' Tumors", cited in European Search Report of EP 09003839.9, (MASI) Massachusetts Inst. Technology, Database Geneseq, WT33 Protein Fragment Sequence # 1, XP-002525441, dated Apr. 12, 2002, 1 page.

Gaiger, A., et al., "Compositions and Methods for WT1 Specific Immunotherapy", cited in European Search Report of EP 04799497.5, Sequence 21 AA; dated Aug. 13, 2002, XP-002473316, 1 page.

Mayumi, T., et al., "Cancer vaccine comprising Cationic liposome and cancer antigen based on tumor suppressor gene WT1", cited in European Search Report of EP 04799497.5, dated Jul. 17, 2003, XP-002473130, 1 page.

Enver Özdemir et al., "HLA-DRB1*0101 and *0405 As Protective Alleles in Japanese Patients With Renal Cell Carcinoma", Cancer Research, vol. 57, No. 4, pp. 742-746, 1997.

Thomas Friede et al., "Natural Ligand Motifs of Closely Related HLA-DR4 Molecules Predict Features of Rheumatoid Arthritis Associated Peptides", Biochimica Et Biophysica Acta, vol. 1316, No. 2, pp. 85-101, 1996.

Hans-Georg Rammensee et al., "MHC Ligands and Peptide Motifs: First Listing", Immunogenetics, vol. 41, No. 4, pp. 178-228, 1995.

Manfred Gessler et al., "Homozygous Deletion in Wilms Tumours of a Zinc-Finger Gene Identified by Chromosome Jumping", Letters to Nature, vol. 343, pp. 774-778, 1990.

Haruo Sugiyama, "Cancer Immunotherapy Targeting WT1 Protein", International Journal of Hematology, vol. 76, pp. 127-132, 2002.

D. Wymann et al., "Human B Cells Secrete Migration Inhibition Factor (MIF) and Present a Naturally Processed MIF Peptide on HLA-DRB1 *0405 by a FXXL Motif", Immunology, vol. 96, pp. 1-9, 1999.

Antonella Maffei et al., "Peptides Bound to Major Histocompatibility Complex Molecules", Peptides, vol. 19, No. 1, pp. 179-198, 1998.

Jung-Hwan Kim, et al., "In Vitro Binding Analysis of Hepatitis B Virus PreS-derived Putative Helper T-cell Epitopes to MHC AS Class II Molecules Using Stable HLA-DRB1 *0405/-DRA*01 01 Transfected Cells", IUBMB Life, vol. 50, 2000, pp. 379-384.

Glenn Y. Ishioka, et al., "Utilization of MHC Class I Transgenic Mice for Development of Minigene DNA Vaccines Encoding Multiple HLA-Restricted CTL Epitopes[1]", The Journal of Immunology, vol. 162, 1999, pp. 3915-3925.

Craig L. Slingluff, Jr. ,et al., "Phase I Trial of a Melanoma Vaccine with gp100 $_{280-288}$ Peptide and Tetanus Helper Peptide in Adjuvant: Immunologic and Clinical Outcomes[1]", Clinical Cancer Research, vol. 7, Oct. 2001, pp. 3012-3024.

Shabnarn Tangri, et al., "Structural Features of Peptide Analogs of Human Histocompatibility Leukocyte Antigen Class I AY Epitopes that Are More Potent and Immunogenic than Wild-Type Peptide", J. Exp. Med., vol. 194, No. 6, 2001, pp. 833-846.

Rena J. May PhD[1]., et al., "CD4+ Peptide Epitopes from the WT1 Oncoprotein Stimulate CD4+ and CD8+ T Cells That Recognize and Kill Leukemia and Solid Tumor Cells" Blood (ASH Annual Meeting Abstracts) 2006, vol. 108: Abstract 3706, 2006 American Society of Hematology. XP009097422, 1 Page.

Ashley John Knights, et al., "Prediction of an HLA-DR-Binding Peptide Derived From Wilms' Tumour 1 Protein and Demonstration of In Vitro Immunogenicity of WT1 (124-138)-Pulsed Dendritic Cells Generated According to an Optimised Protocol", Cancer Immunol Immunother, vol. 51, XP002473128, 2002, pp. 271-281.

Office Action dated Mar. 29, 2016 in Mexican Patent Application No. MX/a/2014/0025956 (with English language translation).

Office Action dated Apr. 7, 2015 in Taiwanese Patent Application No. 100135857 (with English translation).

Combined Chinese Office Action and Search Report dated Apr. 9, 2014 in Patent Application No. 201180058552.2 with English Translation.

Australian Patent Examination Report No. 1 dated Jun. 2, 2014 in Patent Application No. 2011313327.

International Preliminary Report on Patentability dated May 16, 2013 in PCT/JP2011/072874 (English translation only).

International Search Report and Written Opinion of the International Searching Authority dated Dec. 20, 2011 in PCT/JP2011/072874 (English translations only).

Pakistani Office Action dated Jan. 10, 2013 in Patent Application No. 720/2011.

Rena J. May et al., "Peptide Epitopes from the Wilms' Tumor 1 Oncoprotein Stimulate CD4+ and CD8+ T Cells That Recognize and Kill Human Malignant Mesothelioma Tumor Cells", Clinical Cancer Res., vol. 13, No. 15, Aug. 1, 2007, pp. 4547-4555 and 5226 (with cover page).

Fumihiro Fujiki et al., "A WT1 protein-derived, naturally processed 16-mer peptide, WT1$_{332}$, is a promiscuous helper peptide for induction of WT1-specific Th1-type CD4+ T cells", Microbiol Immunal, vol. 52, 2008, pp. 591-600.

Cynthia Lehe et al., "The Wilms' Tumor Antigen Is a Novel Target for Human CD4+ Regulatory T Cells: Implications for Immunotherapy", Cancer Res, vol. 68, No. 15, Aug. 1, 2008, pp. 6350-6359.

Ashley John Knights et al., "Prediction of an HLA-DR-binding peptide derived from Wilms' tumour 1 protein and demonstration of in vitro immunogenicity of WT1(124-138)-pulsed dendritic cells generated according to an optimised protocol", Cancer Immunol Immunother vol. 51, 2002, pp. 271-281.

Ludmil Müller et al., "Synthetic peptides derived from the Wilms' tumor 1 protein sensitize human T lymphocytes to recognize chronic myelogenous leukemia cells", The Hematology Journal, vol. 4, 2003, pp. 57-66.

Daniel A. Haber et al., "An Internal Deletion within an 11p13 Zinc Finger Gene Contributes to the Development of Wilms' Tumor", Cell, vol. 61, Jun. 29, 1990, pp. 1257-1269.

Katherine M. Call et al., "Isolation and Characterization of a Zinc Finger Polypeptide Gene at the Human Chromosome 11 Wilms' Tumor Locus", Cell, vol. 60, Feb. 9, 1990, pp. 509-520.

A.L. Menke et al., "The Wilms' Tumor 1 Gene: Oncogene or Tumor Suppressor Gene?" International Review of Cytology, vol. 181, 1998, pp. 151-212.

Tamotsu Yamagami et al., "Growth Inhibition of Human Leukemic Cells by WT1 (Wilms Tumor Gene) Antisense Oligodeoxynucleotides:

(56) References Cited

OTHER PUBLICATIONS

Implications for the Involvement of WT1 in Leukemogenesis", Blood, vol. 87, No. 7, Apr. 1, 1996, pp. 2878-2884.
Kazushi Inoue et al., "Wilms' Tumor Gene (WT1) Competes With Differentiation-Inducing Signal in Hematopoietic Progenitor Cells", Blood, vol. 91, No. 8, Apr. 15, 1998, pp. 2969-2976.
Akihiro Tsuboi et al., "Constitutive expression of the Wilms' tumor gene WT1 inhibits the differentiation of myeloid progenitor cells but promotes their proliferation in response to granulocyte-colony stimulating factor (G-CSF)", Leukemia Research, vol. 23, 1999, pp. 499-505.
Yoshihiro Oka et al., "Human cytotxic T-lymphocyte responses specific for peptides of the wild-type Wilms' tumor gene (WT1) product", Immunogenetics, vol. 51, 2000, pp. 99-107.
Feng Guang Gao et al., "Antigen-specific $CD4^+$ T-Cell Help Is Required to Activate a Memory $CD8^+$ T Cell to a Fully Functional Tumor Killer Cell", Cancer Research, vol. 62, Nov. 15, 2002, pp. 6438-6441.
Gang Zeng, "MHC Class II-Restricted Tumor Antigens Recognized by the $CD4^+$ T Cells: New Strategies for Cancer Vaccine Design", Journal of Immunotherapy, vol. 24, No. 3, 2001, pp. 195-204.
Office Action dated May 25, 2016 in Mexican Patent Application No. MX/a/2013/003884 (with English language translation).
Combined Chinese Office Action and Search Report dated May 31, 2016 in Patent Application No. 201410573477.9 (with English language translation).
Extended European Search Report dated Jun. 6, 2016 in Patent Application No. 13864968.6.
Office Action dated Feb. 10, 2016 in co-pending U.S. Appl. No. 12/449,765.
Advisory Action (PTOL-303) issued in U.S. Appl. No. 13/755,185 dated Feb. 5, 2015.
Final Rejection issued in U.S. Appl. No. 13/755,185 dated Sep. 25, 2014.
Final Rejection issued in U.S. Appl. No. 10/578,183 dated Dec. 11, 2015.
Final Rejection issued in U.S. Appl. No. 10/578,183 dated May 24, 2012.
Final Rejection issued in U.S. Appl. No. 10/578,183 dated Oct. 12, 2011.
Miscellaneous Action with SSP issued in U.S. Appl. No. 10/578,183 on Dec. 8, 2010.
Non-Final Rejection issued in U.S. Appl. No. 10/578,183 dated Mar. 11, 2015.
Non-Final Rejection issued in U.S. Appl. No. 10/578,183 dated Apr. 26, 2010.
Naylor et al, "Peptide Based Vaccine Approaches for Cancer—A Novel Approach Using a WT-1 Synthetic Long Peptide and the IRX-2 Immunomodulatory Regimen", Cancers (Basel). Dec. 2011; 3(4): 3991-4009.
Kobayashi et al., "Defining MHC class II T helper epitopes for WT1 tumor antigen.", Cancer Immunol Immunother. Jul. 2006;55(7):850-860 cited in the Office Action.
Office Action dated Sep. 6, 2016 in Colombian Patent Application No. 15162173 (with English translation).
Hearing Notice issued May 5, 2016 in Indian Patent Application No. 4956/CHENP/2009.
U.S. Office Action dated Nov. 16, 2016 in co-pending U.S. Appl. No. 12/449,765.
Li-Xin Wang, et al., "Adoptive transfer of tumor-primed, in vitro-activated, $CD4^+$ T effector cells ($T_ES$) combined with $CD8^+$ $T_ES$ provides intratumoral $T_E$ proliferation and synergistic antitumor response" Blood, vol. 109, No. 11, Jun. 1, 2007, pp. 4865-4872.
English Translation of Colombian Office Action dated Sep. 6, 2016 issued in Colombian Patent Application No. 15162173 (Colombian Office Action has already been submitted on Nov. 16, 2016).
Mexican Office Action dated Feb. 26, 2018, issued in the corresponding Mexican Patent Application No. MX/a/2013/003884 (with English Translation).
Russian Office Action dated Jan. 24, 2018, issued in the corresponding Russian Patent Application No. 2014104572/10 (with English Translation).
Lee K.H. et al., Increased Vaccine-Specific T Cell Frequency After Peptide-Based Vaccination Correlates With Increased Susceptibility to In Vitro Stimulation But Does Not Lead to Tumor Regression, The Journal of Immunology, Dec. 1, 1999, 163 (11) 6292-6300 (Cited in the Russian Office Action dated Jan. 24, 2018).
U.S. Office Action dated Dec. 30, 2016, in the co-pending U.S. Appl. No. 14/652,298.
Hailer et al., HLA-DRB1*1301 and *1302 protect against chronic hepatitis B (Journal of Hepatology, 1997; 26: 503-507).
Del Rincón et al., Ethnic Variation in the Clinical Manifestations of Rheumatoid Arthritis; Role of HLA-DRB1 Alleles, Arthritis & Rheumatism, vol. 49, No. 2, Apr. 15, 2003, pp. 200-208.
Nikbin et al., Human Leukocyte Antigen (HLA) Class I and II Polymorphism in Iranian Healthy Population from Yazd Province, Iran J Allergy Asthma Immunol, Feb. 2017, 16(1), pp. 1-13.
Marsh et al., Nomenclature for factors of the HLA system, 2004, Tissue Antigens (2005) 65, pp. 301-369.
Office Action dated Dec. 5, 2016, issued in Eurasian Patent Application No. 201591168 (with its English translation), corresponding to U.S. Appl. No. 14/652,298.
Notice of Allowance and Notice of Allowability dated Jul. 19, 2018, issued in the related U.S. Appl. No. 12/449,765 (10 pages).
Fujiki et al., "A Clear Correlation between WT1-specific Th Response and Clinical Response in WT1 CTL Epitope Vaccination", Anticancer Research 30: 2247-2254 (2010).
Southwood S. et al "Several Common HLA-DR Types Share Largely Overlapping Peptide Binding Repertoires" Journal of Immunology, vol. 160, pp. 3363-3373 (cited in the Office Action dated Mar. 14, 2019 in New Zealand application No. 708990 corresponding to the U.S. Appl. No. 14/652,298 which relates to the present application).

* cited by examiner

[Fig. 1]
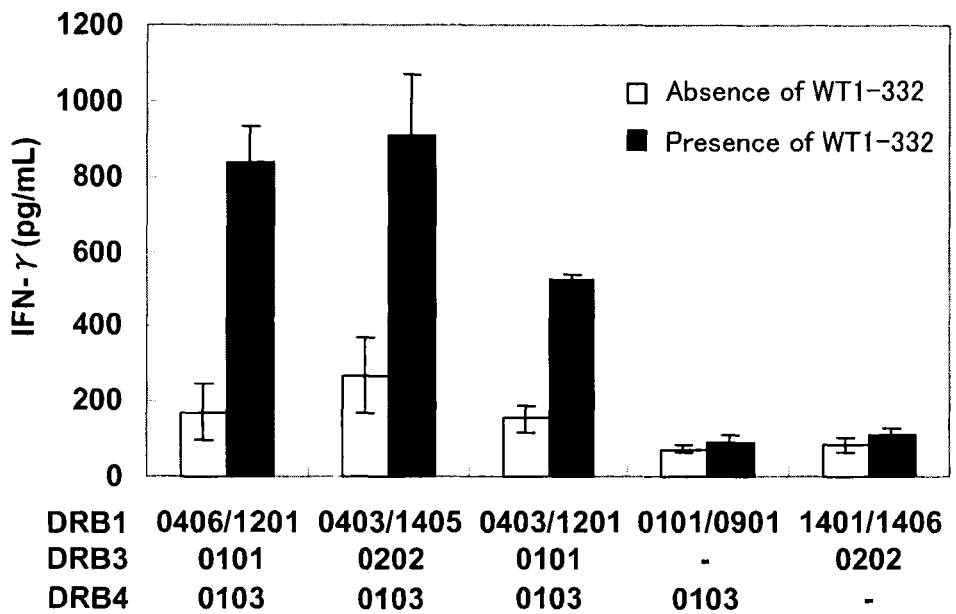
[Fig. 2]
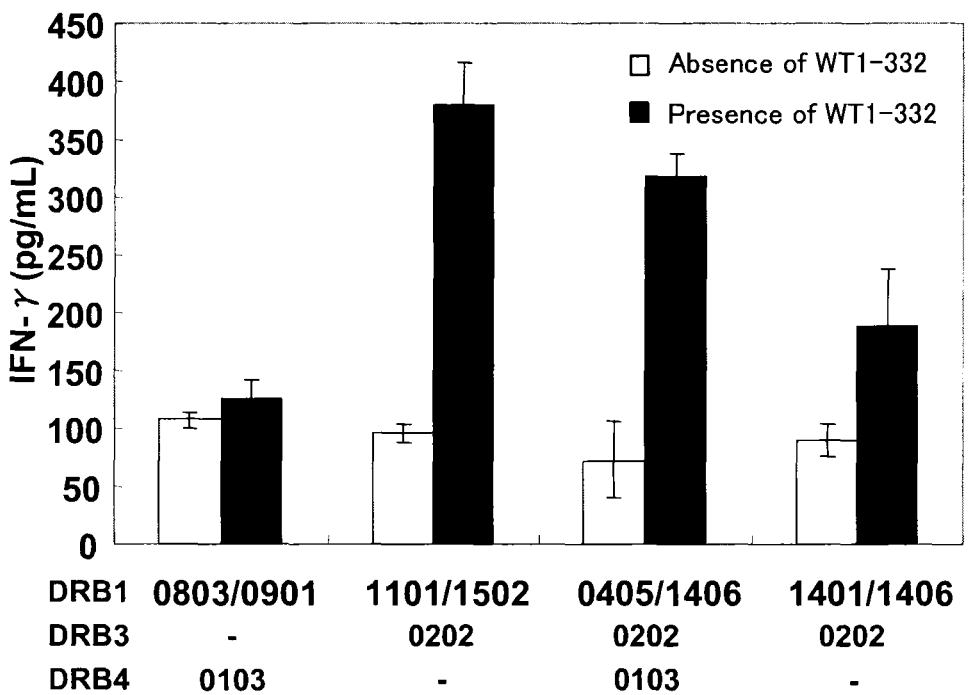

[Fig. 3]
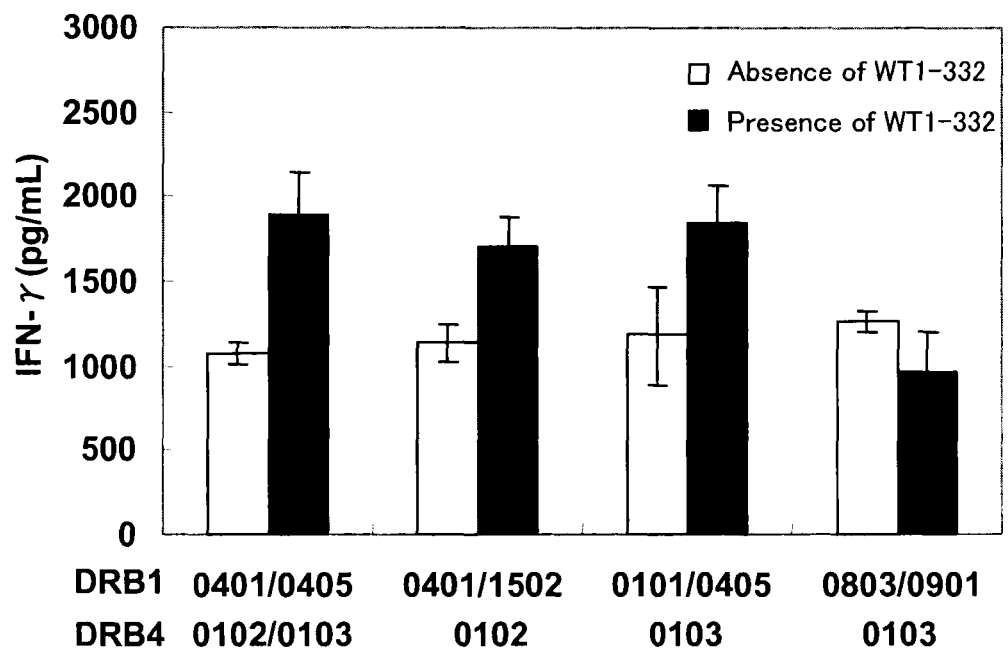
[Fig. 4]
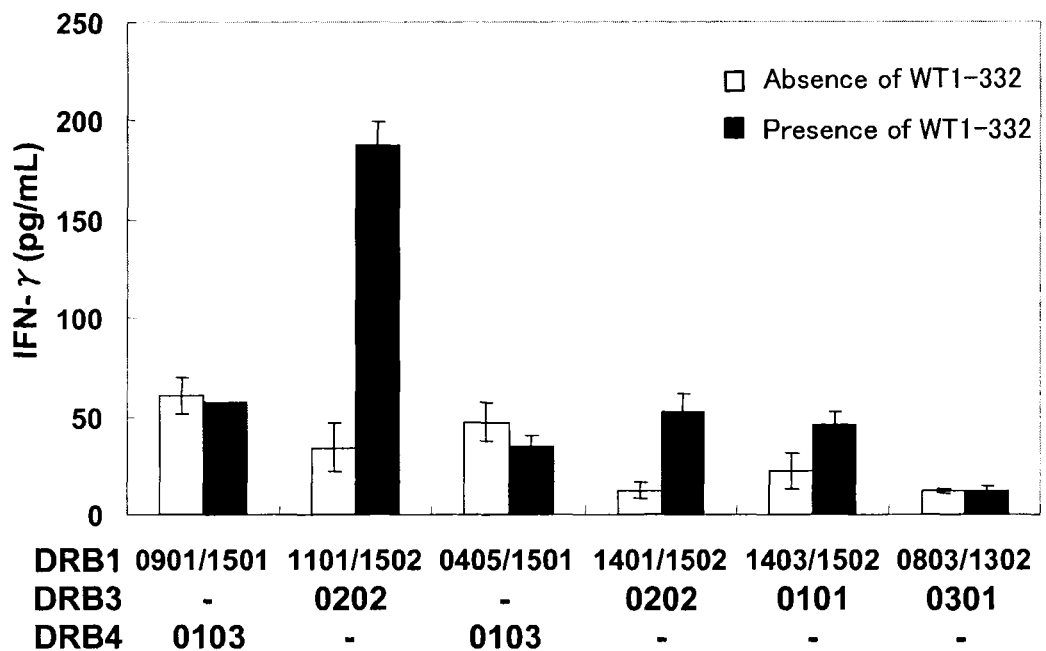

[Fig. 5]
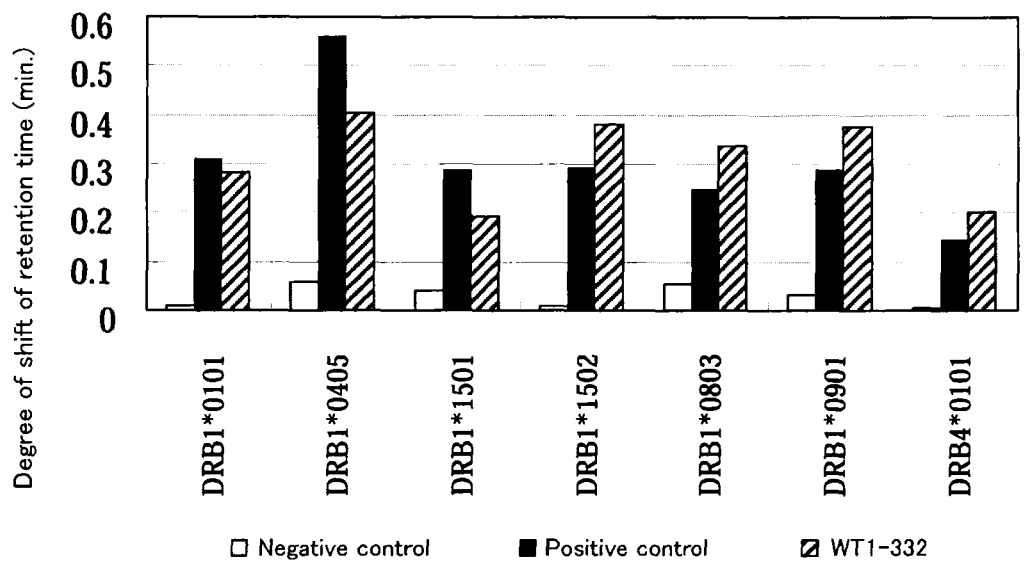
[Fig. 6]
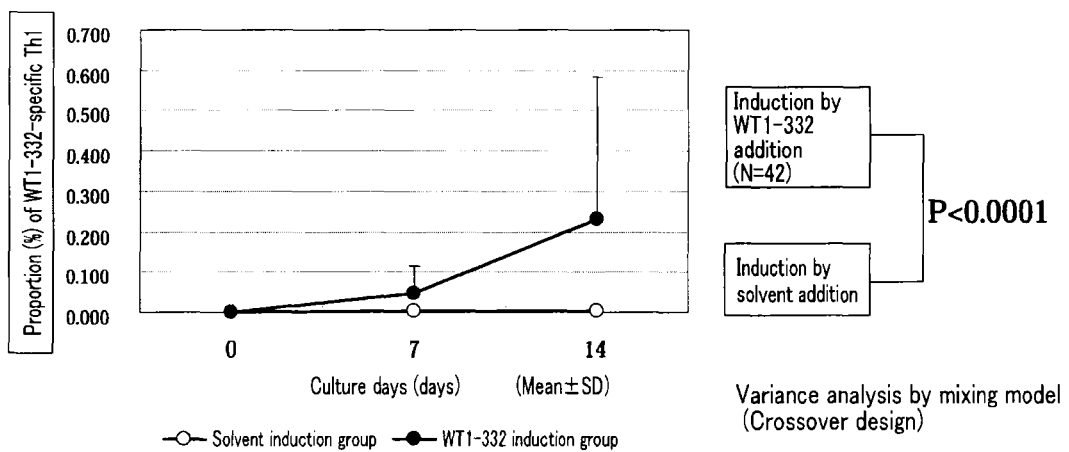

[Fig. 7]
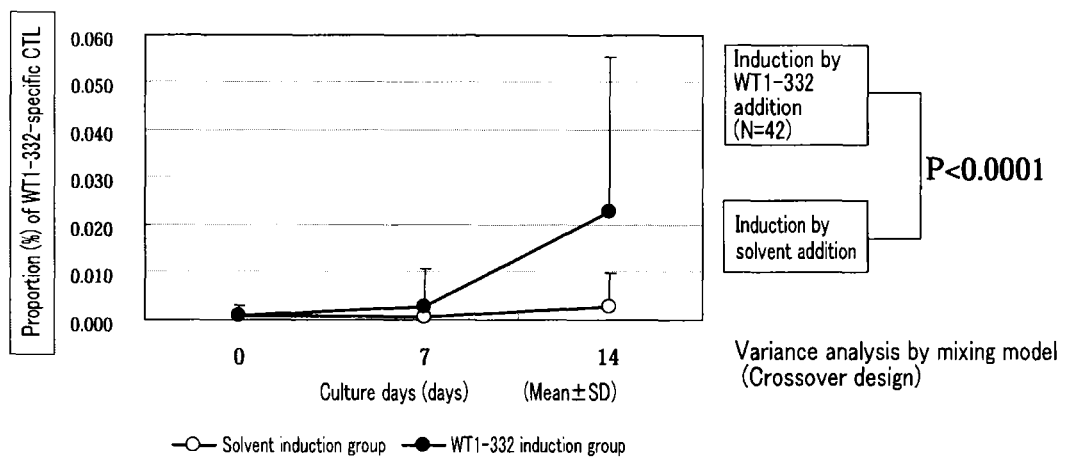
[Fig. 8]
HLA-DR-restrictiveness of WT1-332-induced T cells
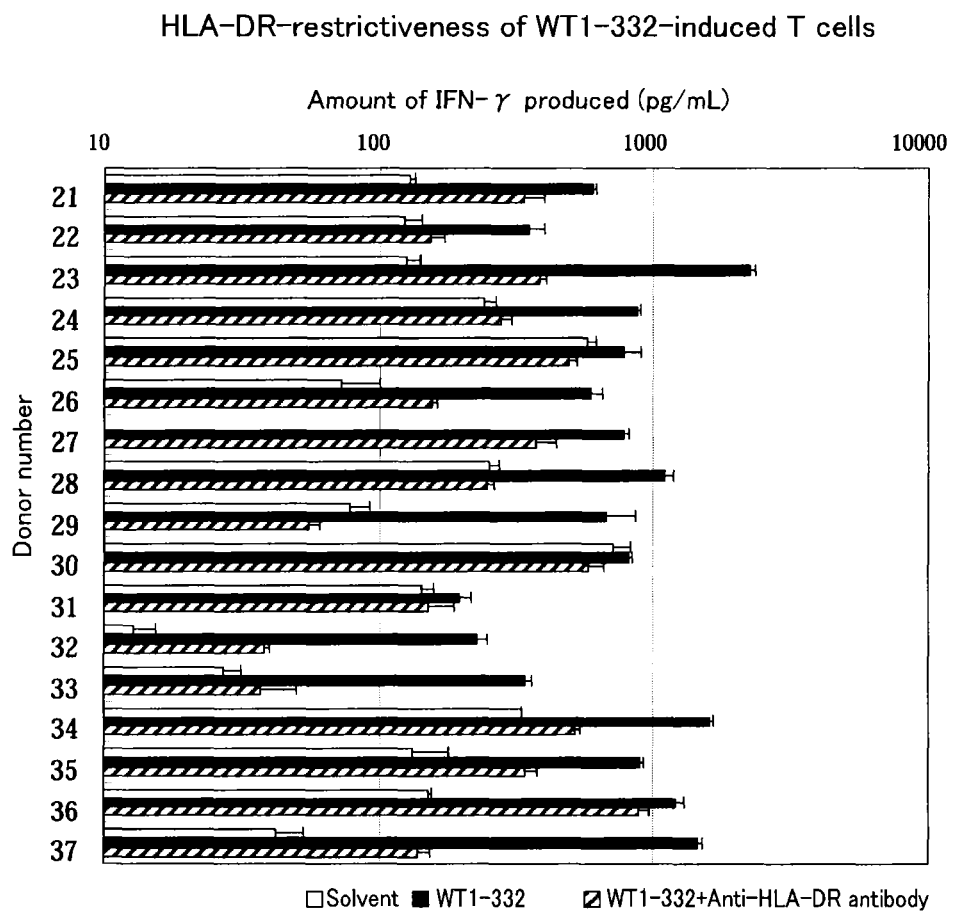

[Fig. 9]
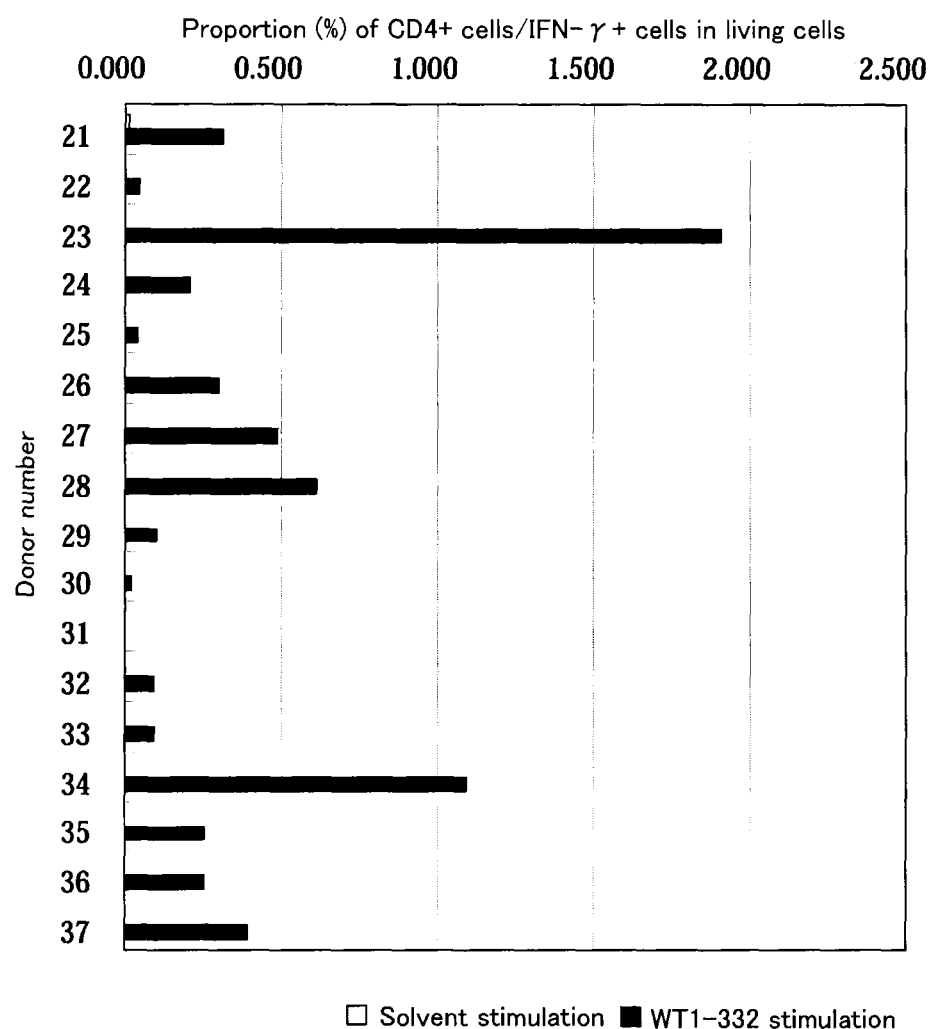

[Fig. 10]
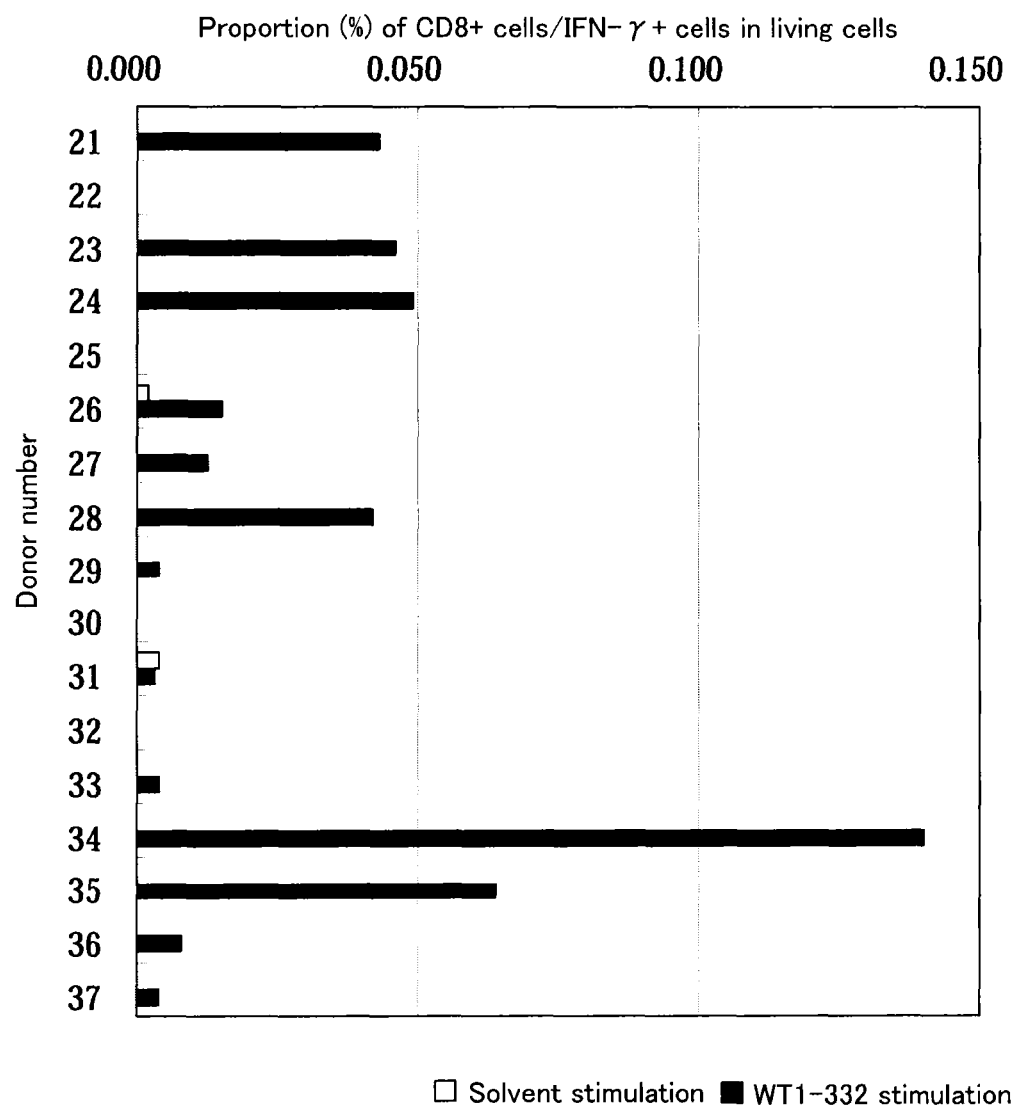

[Fig 11]
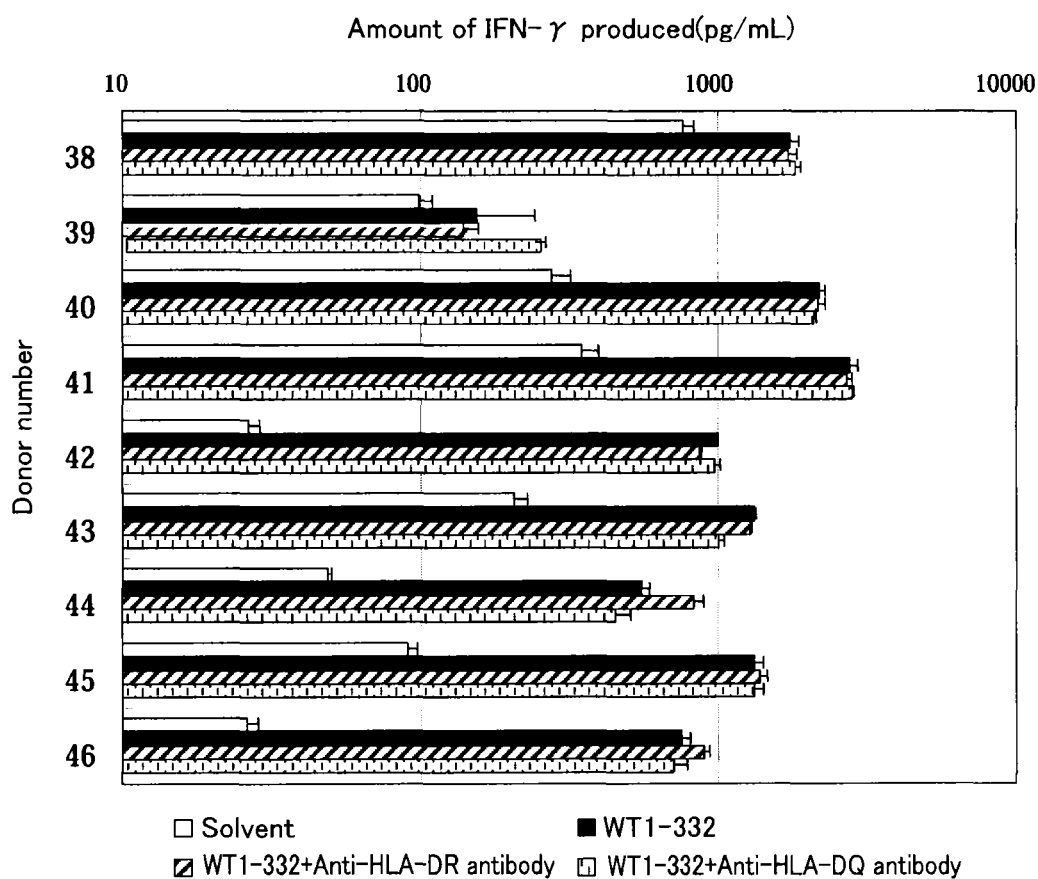

[Fig. 12]
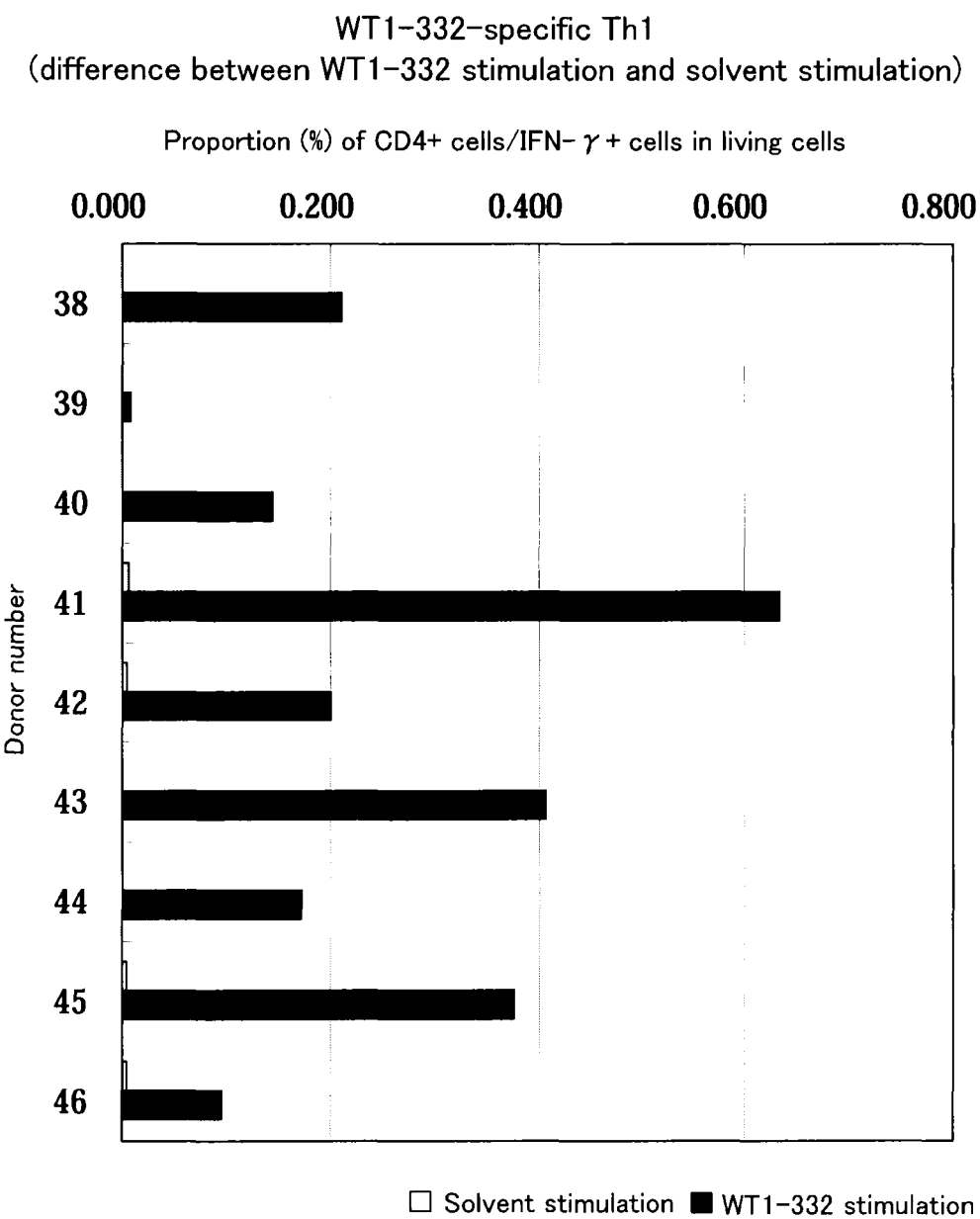

[Fig. 13]
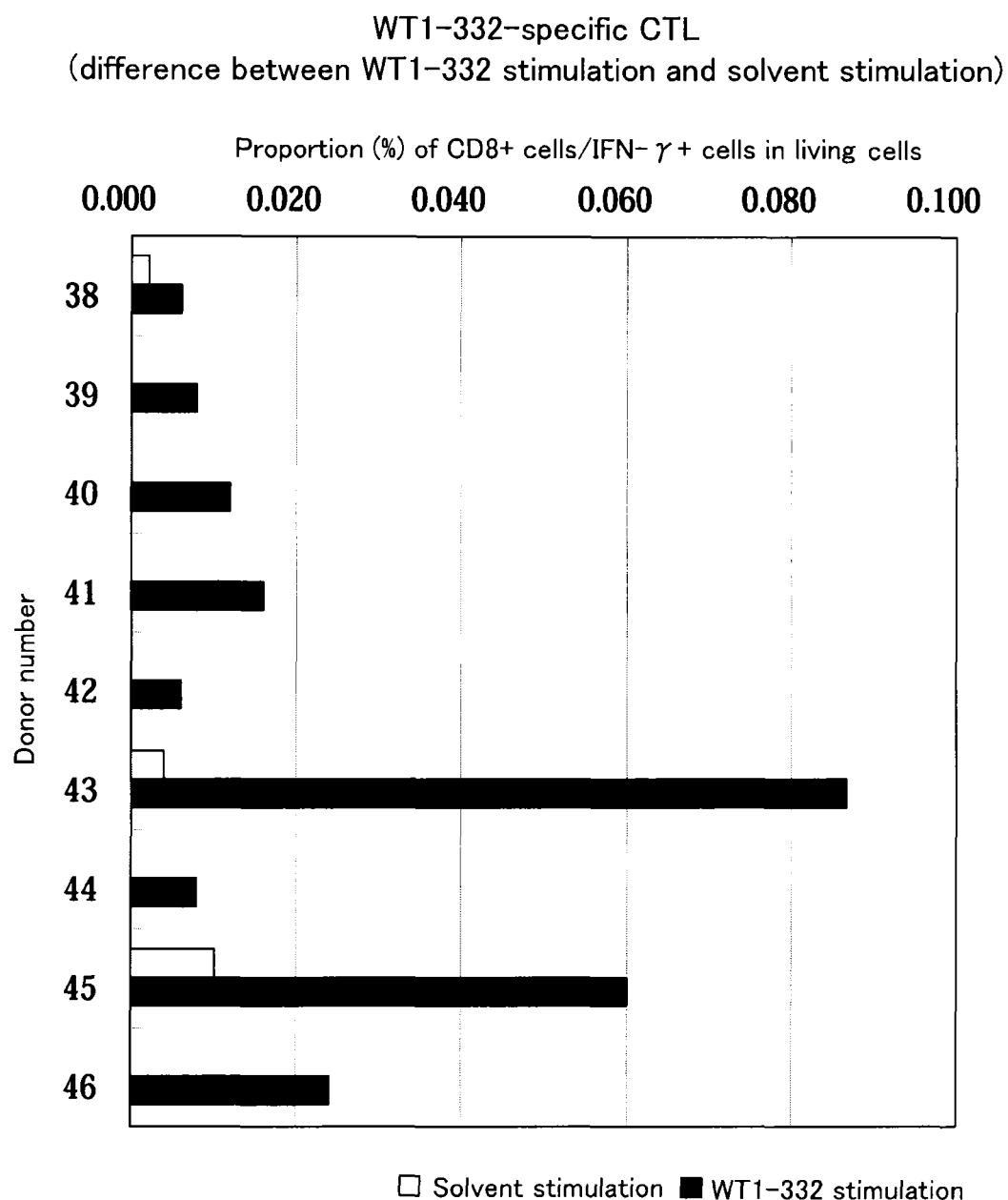

SEQUENCE LISTING

```
<160> NUMBER OF SEQ ID NOS: 4

<210> SEQ ID NO 1
<211> LENGTH: 449
<212> TYPE: PRT
<213> ORGANISM: Homo sapiens

<400> SEQUENCE: 1

Met Gly Ser Asp Val Arg Asp Leu Asn Ala Leu Leu Pro Ala Val Pro
1               5                   10                  15

Ser Leu Gly Gly Gly Gly Gly Cys Ala Leu Pro Val Ser Gly Ala Ala
            20                  25                  30

Gln Trp Ala Pro Val Leu Asp Phe Ala Pro Pro Gly Ala Ser Ala Tyr
        35                  40                  45

Gly Ser Leu Gly Gly Pro Ala Pro Pro Ala Pro Pro Pro Pro
    50                  55                  60

Pro Pro Pro Pro His Ser Phe Ile Lys Gln Glu Pro Ser Trp Gly Gly
65                  70                  75                  80

Ala Glu Pro His Glu Glu Gln Cys Leu Ser Ala Phe Thr Val His Phe
                85                  90                  95

Ser Gly Gln Phe Thr Gly Thr Ala Gly Ala Cys Arg Tyr Gly Pro Phe
            100                 105                 110

Gly Pro Pro Pro Pro Ser Gln Ala Ser Ser Gly Gln Ala Arg Met Phe
        115                 120                 125

Pro Asn Ala Pro Tyr Leu Pro Ser Cys Leu Glu Ser Gln Pro Ala Ile
    130                 135                 140

Arg Asn Gln Gly Tyr Ser Thr Val Thr Phe Asp Gly Thr Pro Ser Tyr
145                 150                 155                 160

Gly His Thr Pro Ser His His Ala Ala Gln Phe Pro Asn His Ser Phe
                165                 170                 175

Lys His Glu Asp Pro Met Gly Gln Gln Gly Ser Leu Gly Glu Gln Gln
            180                 185                 190

Tyr Ser Val Pro Pro Pro Val Tyr Gly Cys His Thr Pro Thr Asp Ser
        195                 200                 205

Cys Thr Gly Ser Gln Ala Leu Leu Leu Arg Thr Pro Tyr Ser Ser Asp
    210                 215                 220
```

```
Asn Leu Tyr Gln Met Thr Ser Gln Leu Glu Cys Met Thr Trp Asn Gln
225                 230                 235                 240

Met Asn Leu Gly Ala Thr Leu Lys Gly Val Ala Ala Gly Ser Ser Ser
            245                 250                 255

Ser Val Lys Trp Thr Glu Gly Gln Ser Asn His Ser Thr Gly Tyr Glu
        260                 265                 270

Ser Asp Asn His Thr Thr Pro Ile Leu Cys Gly Ala Gln Tyr Arg Ile
    275                 280                 285

His Thr His Gly Val Phe Arg Gly Ile Gln Asp Val Arg Arg Val Pro
290                 295                 300

Gly Val Ala Pro Thr Leu Val Arg Ser Ala Ser Glu Thr Ser Glu Lys
305                 310                 315                 320

Arg Pro Phe Met Cys Ala Tyr Pro Gly Cys Asn Lys Arg Tyr Phe Lys
                325                 330                 335

Leu Ser His Leu Gln Met His Ser Arg Lys His Thr Gly Glu Lys Pro
            340                 345                 350

Tyr Gln Cys Asp Phe Lys Asp Cys Glu Arg Arg Phe Ser Arg Ser Asp
        355                 360                 365

Gln Leu Lys Arg His Gln Arg Arg His Thr Gly Val Lys Pro Phe Gln
370                 375                 380

Cys Lys Thr Cys Gln Arg Lys Phe Ser Arg Ser Asp His Leu Lys Thr
385                 390                 395                 400

His Thr Arg Thr His Thr Gly Lys Thr Ser Glu Lys Pro Phe Ser Cys
                405                 410                 415

Arg Trp Pro Ser Cys Gln Lys Lys Phe Ala Arg Ser Asp Glu Leu Val
            420                 425                 430

Arg His His Asn Met His Gln Arg Asn Met Thr Lys Leu Gln Leu Ala
        435                 440                 445

Leu

<210> SEQ ID NO 2
<211> LENGTH: 16
<212> TYPE: PRT
<213> ORGANISM: Homo sapiens

<400> SEQUENCE: 2

Lys Arg Tyr Phe Lys Leu Ser His Leu Gln Met His Ser Arg Lys His
1               5                   10                  15

<210> SEQ ID NO 3
<211> LENGTH: 15
<212> TYPE: PRT
<213> ORGANISM: Artificial
<220> FEATURE:
<223> OTHER INFORMATION: positive control peptide for binding to class
      II monomer protein

<400> SEQUENCE: 3

Pro Val Ser Lys Met Arg Met Ala Thr Pro Leu Leu Met Gln Ala
1               5                   10                  15

<210> SEQ ID NO 4
<211> LENGTH: 16
<212> TYPE: PRT
<213> ORGANISM: Artificial
<220> FEATURE:
<223> OTHER INFORMATION: negative control peptide for binding to class
      II monomer protein

<400> SEQUENCE: 4
```

-continued

```
Lys Ala Glu Arg Ala Asp Leu Ile Ala Tyr Leu Lys Gln Ala Thr Ala
1               5                   10                  15
```

METHOD FOR ACTIVATING HELPER T CELL

TECHNICAL FIELD

The present invention relates to a method for activating helper T cells, which includes the step of activating helper T cells by adding a WT1 peptide to antigen presenting cells, wherein the WT1 peptide has the ability to bind to any MHC class II molecule of an HLA-DRB1*0101 molecule, an HLA-DRB1*0401 molecule, an HLA-DRB1*0403 molecule, an HLA-DRB1*0406 molecule, an HLA-DRB1*0803 molecule, an HLA-DRB1*0901 molecule, an HLA-DRB1*1101 molecule, an HLA-DRB3*0202 molecule, an HLA-DRB4*0101 molecule, an HLA-DRB1*1501 molecule, an HLA-DRB1*0405 molecule, an HLA-DRB1*1502 molecule, an HLA-DPB1*0501 molecule, an HLA-DPB1*0901 molecule, an HLA-DPB1*0201 molecule or an HLA-DPB1*0301 molecule, a composition therefor, a method for activating cytotoxic T cells, an activation inducer of cytotoxic T cells (CTL), a pharmaceutical composition for treating and/or preventing a cancer by activating helper T cells and/or cytotoxic T cells, and the like.

BACKGROUND ART

The WT1 gene (Wilms' tumor 1 gene) was identified as a causative gene of a Wilms' tumor which is a kidney cancer in childhood, and the gene encodes a transcription factor having a zinc finger structure (Non-Patent Documents 1 and 2). Subsequent studies showed that the above gene serves as a cancer gene in hematopoietic organ tumors or solid cancers (Non-Patent Documents 3 to 6).

It was shown that cytotoxic T cells (CTLs) specific to the peptide are induced by stimulating peripheral blood mononuclear cells in vitro using a peptide having a portion of an amino acid sequence encoding the WT1 protein, and these CTLs injure cancer cells of hematopoietic organ tumors or solid cancers expressing the WT1 endogenously. The CTLs recognize the above peptide in the form of a complex bound to an MHC class I molecule, and thus the peptide differs depending on subtypes of the MHC class I (Patent Documents 1 to 4, and Non-Patent Document 7).

On the other hand, the presence of helper T cells specific to a cancer antigen is important in order to induce the CTLs effectively (Non-Patent Document 8). The helper T cells are induced and activated by recognizing a complex of an MHC class II molecule with an antigen peptide on antigen presenting cells. Activated helper T cells aid proliferation, differentiation and maturation of B cells by producing cytokines such as IL-2, IL-4, IL-5, IL-6, or interferons. Since such helper T cells have a function to activate an immune system by promoting proliferation and activation of B cells and T cells, it is suggested that the enhancement of a function of helper T cells through an MHC class II-binding antigen peptide in cancer immunotherapy to enhance effects of a cancer vaccine is useful (Non-Patent Document 9).

It has recently been shown that a promiscuous helper peptide which can bind to multiple MHC class II molecules and activate helper T cells is present among particular peptides having a portion of an amino acid sequence encoding a WT1 protein (hereinafter, also referred to as WT1 peptides in the present specification) (patent documents 5 and 6). However, it was very difficult to verify whether or not the WT1 peptides also have effects on other MHC class II molecules, because of many kinds of MHC class II molecules.

PRIOR ART DOCUMENTS

Patent Documents

Patent Document 1: International Publication No. WO 2003/106682
Patent Document 2: International Publication No. WO 2005/095598
Patent Document 3: International Publication No. WO 2007/097358
Patent Document 4: International Application No. PCT/JP2007/074146
Patent Document 5: International Publication No. WO 2005/045027
Patent Document 6: International Publication No. WO 2008/105462

Non-Patent Documents

Non-Patent Document 1: Daniel A. Haber et al., Cell. 1990 Jun. 29; 61(7):1257-69
Non-Patent Document 2: Call K M et al., Cell. 1990 Feb. 9; 60(3):509-20
Non-Patent Document 3: Menke A L et al., Int Rev Cytol. 1998; 181:151-212. Review
Non-Patent Document 4: Yamagami T et al., Blood. 1996 Apr. 1; 87(7):2878-84
Non-Patent Document 5: Inoue K et al., Blood. 1998 Apr. 15; 91(8):2969-76
Non-Patent Document 6: Tsuboi A et al., Leuk Res. 1999 May; 23(5):499-505
Non-Patent Document 7: Oka Y et al., Immunogenetics. 2000 February; 51(2):99-107
Non-Patent Document 8: Gao F G et al., Cancer Res. 2002 Nov. 15; 62(22):6438-41
Non-Patent Document 9: Zeng G, J. Immunother. 2001 May; 24(3):195-204

DISCLOSURE OF THE INVENTION

Problems to be Solved by the Invention

Accordingly, the object to be achieved by the present invention is to provide a method for activating helper T cells, a method for activating cytotoxic T cells, by applying a particular WT1 peptide to a wide range of MHC class II molecule-positive subjects, an activation inducer of cytotoxic T cells, a pharmaceutical composition for treating/preventing a cancer, and the like.

Means for Solving the Problems

Under these circumstances, the present inventors have intensively studied and found that a peptide having the amino acid sequence: Lys Arg Tyr Phe Lys Leu Ser His Leu Gln Met His Ser Arg Lys His (SEQ ID NO:2) binds to an HLA-DRB1*0101 molecule, an HLA-DRB1*0401 molecule, an HLA-DRB1*0403 molecule, an HLA-DRB1*0406 molecule, an HLA-DRB1*0803 molecule, an HLA-DRB1*0901 molecule, an HLA-DRB1*1101 molecule, an HLA-DRB3*0202 molecule, an HLA-DRB4*0101 molecule, an HLA-DRB1*1501 molecule, an HLA-DRB1*0405 molecule, an HLA-DRB1*1502 molecule, an HLA-DPB1*0501 molecule, an HLA-DPB1*0901 molecule, an HLA-DPB1*0201 molecule, and an HLA-DPB1*0301 molecule, and activates helper T cells and/or cytotoxic T cells. Thus, the present invention has been completed.

The present invention provides:

(1) A method for activating helper T cells, which includes the step of activating helper T cells by adding a WT1 peptide to antigen presenting cells, wherein the WT1 peptide has the ability to bind to any MHC class II molecule of an HLA-DRB1*0101 molecule, an HLA-DRB1*0401 molecule, an HLA-DRB1*0403 molecule, an HLA-DRB1*0406 molecule, an HLA-DRB1*0803 molecule, an HLA-DRB1*0901 molecule, an HLA-DRB1*1101 molecule, an HLA-DRB3*0202 molecule, an HLA-DRB4*0101 molecule, an HLA-DPB1*0201 molecule or an HLA-DPB1*0301 molecule;

(2) The method according to (1), wherein the WT1 peptide has the ability to bind to at least two MHC class II molecules of an HLA-DRB1*0101 molecule, an HLA-DRB1*0401 molecule, an HLA-DRB1*0403 molecule, an HLA-DRB1*0406 molecule, an HLA-DRB1*0803 molecule, an HLA-DRB1*0901 molecule, an HLA-DRB1*1101 molecule, an HLA-DRB3*0202 molecule, an HLA-DRB4*0101 molecule, an HLA-DPB1*0201 molecule and an HLA-DPB1*0301 molecule;

(3) The method according to (1) or (2), wherein the WT1 peptide further has the ability to bind to an HLA-DRB1*0405 molecule, an HLA-DRB1*1501 molecule, an HLA-DRB1*1502 molecule, an HLA-DPB1*0501 molecule and/or an HLA-DPB1*0901 molecule;

(4) The method according to any one of (1) to (3), wherein the addition of a WT1 peptide to antigen presenting cells is carried out by adding a WT1 peptide, a polynucleotide encoding the WT1 peptide, an expression vector containing the polypeptide, or cells containing the expression vector;

(5) The method according to any one of (1) to (4), wherein the WT1 peptide is a peptide containing the amino acid sequence: Lys Arg Tyr Phe Lys Leu Ser His Leu Gln Met His Ser Arg Lys His (SEQ ID NO:2), a variant or a modification thereof;

(6) A composition containing a WT1 peptide for activating helper T cells by adding the WT1 peptide to antigen presenting cells, wherein the WT1 peptide has the ability to bind to any MHC class II molecule of an HLA-DRB1*0101 molecule, an HLA-DRB1*0401 molecule, an HLA-DRB1*0403 molecule, an HLA-DRB1*0406 molecule, an HLA-DRB1*0803 molecule, an HLA-DRB1*0901 molecule, an HLA-DRB1*1101 molecule, an HLA-DRB3*0202 molecule, an HLA-DRB4*0101 molecule, an HLA-DPB1*0201 molecule or an HLA-DPB1*0301 molecule;

(7) The composition according to (6), wherein the WT1 peptide has the ability to bind to at least two MHC class II molecules of an HLA-DRB1*0101 molecule, an HLA-DRB1*0401 molecule, an HLA-DRB1*0403 molecule, an HLA-DRB1*0406 molecule, an HLA-DRB1*0803 molecule, an HLA-DRB1*0901 molecule, an HLA-DRB1*1101 molecule, an HLA-DRB3*0202 molecule, an HLA-DRB4*0101 molecule, an HLA-DPB1*0201 molecule and an HLA-DPB1*0301 molecule;

(8) The composition according to (6) or (7), wherein the WT1 peptide further has the ability to bind to an HLA-DRB1*0405 molecule, an HLA-DRB1*1501 molecule, an HLA-DRB1*1502 molecule, an HLA-DPB1*0501 molecule and/or an HLA-DPB1*0901 molecule;

(9) The composition according to any one of (6) to (8), wherein the addition of a WT1 peptide to antigen presenting cells is carried out by adding a WT1 peptide, a polynucleotide encoding the WT1 peptide, an expression vector containing the polynucleotide, or cells containing the expression vector;

(10) The composition according to any one of (6) to (9), wherein the WT1 peptide is a peptide containing the amino acid sequence: Lys Arg Tyr Phe Lys Leu Ser His Leu Gln Met His Ser Arg Lys His (SEQ ID NO:2), a variant or a modification thereof;

(11) Antigen presenting cells which present a complex of an antigen peptide containing a WT1 peptide with an MHC class II molecule, wherein the MHC class II molecule is any MHC class II molecule of an HLA-DRB1*0101 molecule, an HLA-DRB1*0401 molecule, an HLA-DRB1*0403 molecule, an HLA-DRB1*0406 molecule, an HLA-DRB1*0803 molecule, an HLA-DRB1*0901 molecule, an HLA-DRB1*1101 molecule, an HLA-DRB3*0202 molecule, an HLA-DRB4*0101 molecule, an HLA-DPB1*0201 molecule or an HLA-DPB1*0301 molecule;

(12) Helper T cells which recognize a complex of an antigen peptide containing a WT1 peptide with an MHC class II molecule, wherein the MHC class II molecule is any MHC class II molecule of an HLA-DRB1*0101 molecule, an HLA-DRB1*0401 molecule, an HLA-DRB1*0403 molecule, an HLA-DRB1*0406 molecule, an HLA-DRB1*0803 molecule, an HLA-DRB1*0901 molecule, an HLA-DRB1*0101 molecule, an HLA-DRB3*0202 molecule, an HLA-DRB4*0101 molecule, an HLA-DPB1*0201 molecule or an HLA-DPB1*0301 molecule;

(13) Cytotoxic T cells which are activated by the helper T cells according to (11);

(14) A pharmaceutical composition for treating or preventing a cancer, including, as an active ingredient, any of the composition according to any one of (6) to (10), the antigen presenting cells according to (11), the helper T cells according to (12), or the cytotoxic T cells according to (13);

(15) A pharmaceutical composition for activating cytotoxic T cells, including, as an active ingredient, any of a WT1 peptide, a polynucleotide encoding the WT1 peptide, an expression vector containing the polynucleotide, or cells containing the expression vector, and which is administered to a subject having any MHC class II molecule of an HLA-DPB1*0501 molecule, an HLA-DPB1*0901 molecule, an HLA-DPB1*0201 molecule, an HLA-DPB1*0301 molecule, an HLA-DRB1*1501 molecule, an HLA-DRB1*1502 molecule, an HLA-DRB1*0405 molecule, an HLA-DRB1*0101 molecule, an HLA-DRB1*0401 molecule, an HLA-DRB1*0403 molecule, an HLA-DRB1*0406 molecule, an HLA-DRB1*0803 molecule, an HLA-DRB1*0901 molecule, an HLA-DRB1*1101 molecule, an HLA-DRB3*0202 molecule or an HLA-DRB4*0101 molecule;

(16) An antibody specifically binding to a WT1 peptide, wherein the WT1 peptide has the ability to bind to any MHC class II molecule of an HLA-DRB1*0101 molecule, an HLA-DRB1*0401 molecule, an HLA-DRB1*0403 molecule, an HLA-DRB1*0406 molecule, an HLA-DRB1*0803 molecule, an HLA-DRB1*0901 molecule, an HLA-DRB1*1101 molecule, an HLA-DRB3*0202 molecule, an HLA-DRB4*0101 molecule, an HLA-DPB1*0201 molecule or an HLA-DPB1*0301 molecule;

(17) A method for determining the presence or amount of WT1-specific helper T cells in a subject positive in respect to any MHC class II molecule of an HLA-DRB1*0101, HLA-DRB1*0401, HLA-DRB1*0403, HLA-DRB1*0406, HLA-DRB1*0803, HLA-DRB1*0901, HLA-DRB1*1101, HLA-DRB3*0202, HLA-DRB4*0101, HLA-DPB1*0201 molecule or an HLA-DPB1*0301 molecule, the method includes the steps of:

(a) stimulating a sample obtained from the subject using a WT1 peptide, and (b) determining the presence or amount of cytokines or helper T cells, wherein the increase of the presence or amount of cytokines or helper T cells shows the presence or amount of the WT1-specific helper T cells.

EFFECTS OF THE INVENTION

According to the present invention, a method for activating helper T cells, a composition therefor, a method for activating cytotoxic T cells, a composition therefor, an activation inducer of cytotoxic T cells, a pharmaceutical composition for treating and/or preventing a cancer by activating helper T cells and cytotoxic T cells, and the like are obtained by applying a WT1 peptide to a wide range of subjects having any MHC class II molecule of an HLA-DRB1*0101 molecule, an HLA-DRB1*0401 molecule, an HLA-DRB1*0403 molecule, an HLA-DRB1*0406 molecule, an HLA-DRB1*0803 molecule, an HLA-DRB1*0901 molecule, an HLA-DRB1*1101 molecule, an HLA-DRB3*0202 molecule, an HLA-DRB4*0101 molecule, an HLA-DRB1*1501 molecule, an HLA-DRB1*0405 molecule, an HLA-DRB1*1502 molecule, an HLA-DPB1*0501 molecule, an HLA-DPB1*0901 molecule, an HLA-DPB1*0201 molecule or an HLA-DPB1*0301 molecule, thus enabling activation of helper T cells and cytotoxic T cells in vivo and in vitro in subjects having such an MHC class II molecule, and treatment and prevention of a cancer, and the like.

BRIEF DESCRIPTION OF THE DRAWINGS

FIG. 1 shows the results obtained by measuring the amount of IFN-γ after co-culturing T cells induced from PBMCs derived from donor 1 (HLA-DRB1*0406/1201-, DRB3*0101-, and DRB4*0103-positive) with PBMCs derived from various donors pulsed with WT1-332. In the drawing, the ordinate denotes the amount of IFN-γ (pg/mL) in a supernatant liquid after the co-culture. In the drawing, the abscissa denotes the types of HLA-DRB1, 3 and 4 molecules which are positive in the various donors.

FIG. 2 shows the results obtained by measuring the amount of IFN-γ after co-culturing T cells induced from PBMCs derived from donor 2 (HLA-DRB1*0901/1101-, DRB3*0202-, and DRB4*0103-positive) with PBMCs derived from various donors pulsed with WT1-332. In the drawing, the ordinate denotes the amount of IFN-γ (pg/mL) in a supernatant liquid after the co-culture. The abscissa denotes the types of HLA-DRB1, 3 and 4 molecules which are positive in the various donors.

FIG. 3 shows the results obtained by measuring the amount of IFN-γ after co-culturing T cells induced from PBMCs derived from donor 3 (HLA-DRB1*0401/0405-, and DRB4*0102/0103-positive) with PBMCs derived from various donors pulsed with WT1-332. In the drawing, the ordinate denotes the amount of IFN-γ (pg/mL) in a supernatant liquid after the co-culture. The abscissa denotes the types of HLA-DRB1 and 4 molecules which are positive in the various positive donors.

FIG. 4 shows the results obtained by measuring the amount of IFN-γ after co-culturing T cells induced from PBMCs derived from donor 4 (HLA-DRB1*0901/1101-, DRB3*0202-, and DRB4*0103-positive) with PBMCs derived from various donors pulsed with WT1-332. In the drawing, the ordinate denotes the amount of IFN-γ (pg/mL) in a supernatant liquid after the co-culture. The abscissa denotes the types of HLA-DRB1, 3 and 4 molecules which are positive in the various positive donors.

FIG. 5 shows that HLA-class II monomer proteins (DRB1*0101, DRB1*0405, DRB1*1501, DRB1*1502, DRB1*0803, DRB1*0901 and DRB4*0101) were specifically associated with various peptides. In the drawing, the ordinate denotes the degree of shift of retention time (minute). The abscissa denotes the types of HLA-class II monomer proteins. Also, the bar graphs show the types of peptides added [from the left, negative control (□), positive control (■), and WT1-332 (shaded □)].

FIG. 6 shows that the proportion of WT1-332-specific Th1 (the proportion of CD4-positive cells/intracellular IFN-γ-positive cells) increases time-dependently and significantly when T cells induced from PBMCs derived from healthy blood donors (in total 42 donors having at least one of HLA-DRB1*1501, 1502, 0405, HLA-DPB1*0501, and 0901) were stimulated with WT1-332. In the drawing, the ordinate denotes the proportion (%) of the number of CD4-positive cells/the number of intracellular IFN-γ-positive cells in living cells, and the abscissa denotes culture days (days). Also, the symbol "●" denotes the proportion in samples induced by addition of WT1-332 (WT1-332 induction group), and the symbol "○" denotes the proportion in samples induced by addition of a solvent (control) (solvent induction group).

FIG. 7 shows that the number of WT1-332-specific CTL cells (the proportion of CD8-positive cells/IFN-γ-positive cells) increases time-dependently and significantly when T cells induced from PBMCs derived from healthy blood donors (in total 42 donors having at least one of HLA-DRB1*1501, 1502, 0405, HLA-DPB1*0501, and 0901) were stimulated with WT1-332. In the drawing, the ordinate denotes the proportion (%) of the number of CD8-positive cells/the number of intracellular IFN-γ-positive cells in living cells, and the abscissa denotes culture days (days). Also, the symbol "●" denotes the proportion in samples induced by addition of WT1-332 (WT1-332 induction group), and the symbol "○" denotes the proportion in samples induced by addition of a solvent (control) (solvent induction group).

FIG. 8 shows HLA-DR-restrictiveness of 17 samples (donors 21 to 37) in which WT1-332-specific Th1 was induced in FIG. 6 and FIG. 7. In each sample, a WT1-332-specific IFN-γ production was recognized when T cells on day 14 after induction by WT1-332 addition were stimulated with WT1-332, and the IFN-γ production was inhibited when the cells were cultured with addition of an anti-HLA-DR antibody. This shows that the T cells induced by WT1-332 are HLA-DR-restricted. In the drawing, the ordinate denotes the donor number (donors 21 to 37), and the abscissa denotes the amount of IFN-γ produced (pg/mL). Also, the symbol "■" denotes the amount of IFN-γ produced after WT1-332 stimulation, the symbol "shaded □" denotes the amount of IFN-γ produced after WT1-332+anti-HLA- DR antibody stimulation, and the symbol "☐" denotes the amount of IFN-γ produced after solvent (control) stimulation.

FIG. 9 shows that the proportion of the number of WT1-332-specific Th1 cells (CD4-positive cells/intracellular IFN-γ-positive cells) increases when T cells on day 14 after induction by WT1-332 addition are stimulated with WT1-332 in each of 17 samples (donors 21 to 37) having HLA-DR-restricted WT1-332-specific Th1 induced in FIG. 6 and FIG. 7. In the drawing, the ordinate denotes the donor number (donors 21 to 37), and the abscissa denotes the proportion (%) of the number of CD4-positive cells/the number of intracellular IFN-γ-positive cells in living cells. Also, the symbol "■" denotes the proportion after WT1-332 stimulation, and the symbol "☐" denotes the proportion after solvent (control) stimulation.

FIG. 10 shows that the proportion of the number of WT1-332-specific CTL cells (CD8-positive cells/intracellular IFN-γ-positive cells) increases when T cells on day 14 after induction by WT1-332 addition are stimulated with WT1-332 in each of 17 samples (donors 21 to 37) having HLA-DR-restricted WT1-332-specific Th1 induced in FIG. 6 and FIG. 7. In the drawing, the ordinate denotes the donor number (donors 21 to 37), and the abscissa denotes the proportion (%) of the number of CD8-positive cells/the number of intracellular IFN-γ-positive cells in living cells. Also, the symbol "■" denotes the proportion after WT1-332 stimulation, and the symbol "☐" denotes the proportion after solvent (control) stimulation.

FIG. 11 shows HLA-DP-restrictiveness of 9 samples (donors 38 to 46) in which WT1-332-specific Th1 was induced in FIG. 6 and FIG. 7. In each sample, a WT1-332-specific IFN-γ production was recognized when T cells on day 14 after induction by WT1-332 addition were stimulated with WT1-332, and the IFN-γ production was not inhibited when the cells were cultured with addition of an anti-HLA-DR antibody, and also when the cells were cultured with addition of an anti-HLA-DQ antibody. This shows that the T cells induced by WT1-332 are HLA-DP-restricted. In the drawing, the ordinate denotes the donor number (donors 38 to 46), and the abscissa denotes the amount of IFN-γ produced (pg/mL). Also, the symbol "■" denotes the amount of IFN-γ produced after WT1-332 stimulation, the symbol "shaded ☐" denotes the amount of IFN-γ produced after WT1-332+anti-HLA-DR antibody stimulation, the symbol "dashed ☐" denotes the amount of IFN-γ produced after WT1-332+anti-HLA-DQ antibody stimulation, and the symbol "☐" denotes the amount of IFN-γ produced after solvent (control) stimulation.

FIG. 12 shows that the proportion of the number of WT1-332-specific Th1 cells (CD4-positive cells/intracellular IFN-γ-positive cells) increases when T cells on day 14 after induction by WT1-332 addition are stimulated with WT1-332 in each of 9 samples (donors 38 to 46) having HLA-DP-restrictive WT1-332-specific Th1 induced in FIG. 6 and FIG. 7. In the drawing, the ordinate denotes the donor number (donors 38 to 46), and the abscissa denotes the proportion (%) of the number of CD4-positive cells/the number of intracellular IFN-γ-positive cells in living cells. Also, the symbol "■" denotes the proportion after WT1-332 stimulation, and the symbol "☐" denotes the proportion after solvent (control) stimulation.

FIG. 13 shows that the proportion of the number of WT1-332-specific CTL cells (CD8-positive cells/intracellular IFN-γ-positive cells) increases when T cells on day 14 after induction by WT1-332 addition are stimulated with WT1-332 in each of 9 samples (donors 38 to 46) having HLA-DP-restricted WT1-332-specific Th1 induced in FIG. 6 and FIG. 7. In the drawing, the ordinate denotes the donor number (donors 38 to 46), and the abscissa denotes the proportion (%) of the number of CD8-positive cells/the number of intracellular IFN-γ-positive cells in living cells. Also, the symbol "■" denotes the proportion after WT1-332 stimulation, and the symbol "☐" denotes the proportion after solvent (control) stimulation.

MODES FOR CARRYING OUT THE INVENTION

In one aspect, the present invention provides a method for activating helper T cells or cytotoxic T cells, which includes the step of activating helper T cells or cytotoxic T cells by adding a WT1 peptide to antigen presenting cells, wherein the WT1 peptide has the ability to bind to an MHC class II molecule. In the present invention, the step of activating cytotoxic T cells may be carried out by passing through the step of activating helper T cells. Also, the WT1 peptide used in the present invention is one having the ability to bind to any MHC class II molecule of an HLA-DRB1*0101 molecule, an HLA-DRB1*0401 molecule, an HLA-DRB1*0403 molecule, an HLA-DRB1*0406 molecule, an HLA-DRB1*0803 molecule, an HLA-DRB1*0901 molecule, an HLA-DRB1*1101 molecule, an HLA-DRB3*0202 molecule, an HLA-DRB4*0101 molecule, an HLA-DRB1*1501 molecule, an HLA-DRB1*0405 molecule, an HLA-DRB1*1502 molecule, an HLA-DPB1*0501 molecule, an HLA-DPB1*0901 molecule, an HLA-DPB1*0201 molecule or an HLA-DPB1*0301 molecule. Moreover, the WT1 peptide used in the present invention may be one having the ability to bind to at least two or more MHC class II molecules of the above MHC class II molecules. Also, the WT1 peptide used in the present invention may have the ability to bind to any MHC class II molecule, for example, of HLA-DR, HLA-DQ and HLA-DP molecules.

In the present invention, the WT1 peptide may be a peptide having a portion of an amino acid sequence of a human WT1 protein depicted in SEQ ID NO:1. The peptide according to the present invention has no particular limitation in its amino acid sequence and length so far as the peptide has the above feature. However, a too long peptide is susceptible to a protease action, and a too short peptide can not bind to a peptide accommodating groove well. The length of the peptide according to the present invention is one of preferably 10 to 25 amino acids, more preferably 15 to 21 amino acids, further preferably 16 to 20 amino acids, for example, of 16 amino acids, 17 amino acids, 18 amino acids, or 19 amino acids. Specific examples of the peptide according to the present invention are those containing the amino acid sequence: Lys Arg Tyr Phe Lys Leu Ser His Leu Gln Met His Ser Arg Lys His (SEQ ID NO:2).

In addition, the WT1 peptide used in the present invention includes variants of the above peptide. The variants may contain, for example, a peptide selected from the group consisting of peptides having an amino acid sequence in which several amino acids, for example, 1 to 9, preferably 1 to 5, 1 to 4, 1 to 3, more preferably 1 to 2 amino acids, further preferably one amino acid in the amino acid sequence depicted in SEQ ID NO:2 is/are substituted, deleted or added. Substitution of amino acids in peptides may be carried out at any positions and with any types of amino acids, and conservative amino acid substitution is preferred. Examples of the conservative amino acid substitution include substitution of a Glu residue with an Asp residue, a Phe residue with a Tyr residue, a Leu residue with an Ile residue, an Ala residue with a Ser residue, a His residue with an Arg residue and the like. Preferably, addition or deletion of amino acids may be carried out at the N-terminus and the C-terminus in peptides, but may be carried out in an interior sequence. Preferred specific examples of the peptides according to the present invention are those having SEQ ID NO:2. In this connection, any of the above peptides must have the ability to bind to any MHC class II molecule of an HLA-DRB1*0101 molecule, an HLA-DRB1*0401 molecule, an HLA-DRB1*0403 molecule, an HLA-DRB1*0406 molecule, an HLA-DRB1*0803 molecule, an HLA-DRB1*0901 molecule, an HLA-DRB1*1101 molecule, an HLA-DRB3*0202 molecule, an HLA-DRB4*0101 molecule, an HLA-DRB1*1501 molecule, an HLA-DRB1*0405 molecule, an HLA-DRB1*1502 molecule, an HLA-DPB1*0501 molecule, an HLA-DPB1*0901 molecule, an HLA-DPB1*0201 molecule or an HLA-DPB1*0301 molecule, and must activate helper T cells or cytotoxic T cells (herein, also referred to as CTL). In the present specification, the above WT1 peptide is also referred to as "WT1-332". Also, human MHC molecules are generally referred to as HLA molecules, and therefore, MHC is used as a synonym of HLA in the present specification.

Moreover, the peptides according to the present invention may be those obtained by modification of the above amino acid sequence. Amino acid residues in the above amino acid sequence can be modified by a known method. Such modification may be, for example, esterification, alkylation, halogenation, phosphorylation and the like on a functional group in a side chain of an amino acid residue. Also, it is possible to bind various substances to the N-terminus and/or C-terminus of a peptide containing the above amino acid sequence. For example, an amino acid, a peptide, an analog thereof and the like may be bound to the peptide. For example, a histidine tag may be added, or a fusion protein may be formed together with a protein such as thioredoxin. Alternatively, a detectable label may be bound to the WT1 peptide. In case these substances are bound to the peptide according to the present invention, they may be treated, for example, by an in vivo enzyme and the like, or by a process such as intracellular processing to finally generate a peptide consisting of the above amino acid sequence, which is presented on cell surface as a complex with an MHC class II molecule, thereby being able to obtain an induction effect of helper T cells and/or cytotoxic T cells. These substances may be those regulating solubility of the peptide according to the present invention, those improving stability of the peptide such as protease resistance, those allowing specific delivery of the peptide of the present invention, for example, to a given tissue or organ, or those having an enhancing action of an uptake efficiency of antigen presenting cells or other action. Also, these substances may be those increasing an ability to induce CTL, for example, helper peptides other than the peptide according to the present invention.

The WT1 peptide used in the present invention can be synthesized using a method usually used in the art or a modified method thereof. Such a synthesis method is disclosed, for example, in Peptide Synthesis, Interscience, New York, 1966; The Proteins, Vol. 2, Academic Press Inc., New York, 1976; Peptide Synthesis, Maruzen Co., Ltd., 1975; Basis and Experiments of Peptide Synthesis, Maruzen Co., Ltd., 1985; Development of Medicines (continuation), Vol. 14, Peptide Synthesis, Hirokawa Shoten Co., 1991, and the like. Also, the peptide used in the present invention can be prepared using a genetic engineering technique on the basis of information of a nucleotide sequence encoding the peptide. Such a genetic engineering technique is well known to those skilled in the art. Such a technique can be conducted according to methods such as those described in literatures (Molecular Cloning, T. Maniatis et al., CSH Laboratory (1983); DNA Cloning, DM. Glover, IRL PRESS (1985)).

Also, the present invention relates to a polynucleotide sequence encoding the WT1 peptide described above. The polynucleotide sequence encoding the WT1 peptide may be a DNA sequence or an RNA sequence. In the present invention, such a polynucleotide sequence may be used instead of the WT1 peptide. Such a polynucleotide sequence may be used by integrating into a suitable vector. The vector includes plasmids, phage vectors, virus vectors and the like, for example, pUC118, pUC119, pBR322, pCR3, pYES2, pYEUra3, pKCR, pCDM8, pGL2, pcDNA3.1, pRc/RSV, pRc/CMV, pAcSGHisNT-A, λZAPII, λgt11 and the like. The vector may contain, as needed, factors such as an expression-inducible promoter, a gene encoding a signal sequence, a marker gene for selection, and a terminator. A method for introducing these genes into cells or living bodies, a method for expressing them and the like are known to those skilled in the art.

The antigen presenting cells used in the present invention are those which can present an antigen peptide containing the above WT1 peptide together with an MHC class II molecule to helper T cells, and mean, for example, dendritic cells, peripheral blood mononuclear cells and the like. Accordingly, subjects from which the antigen presenting cells used in the present invention are derived must have the same molecule as an MHC class II molecule to which the WT1 peptide added can bind (for example, any one or more MHC class II molecules of an HLA-DRB1*0101 molecule, an HLA-DRB1*0401 molecule, an HLA-DRB1*0403 molecule, an HLA-DRB1*0406 molecule, an HLA-DRB1*0803 molecule, an HLA-DRB1*0901 molecule, an HLA-DRB1*1101 molecule, an HLA-DRB3*0202 molecule, an HLA-DRB4*0101 molecule, an HLA-DRB1*1501 molecule, an HLA-DRB1*0405 molecule, an HLA-DRB1*1502 molecule, an HLA-DPB1*0501 molecule, an HLA-DPB1*0901 molecule, an HLA-DPB1*0201 molecule, an HLA-DPB1*0301 molecule, etc.).

In the present invention, addition of the WT1 peptide to antigen presenting cells may be carried out directly by addition of the WT1 peptide, or indirectly by addition of a polynucleotide encoding the WT1 peptide or of an expression vector containing a polynucleotide encoding the WT1 peptide or by addition of cells containing the expression vector. The above addition can be carried out by a method known in the art. The above polynucleotide encoding the WT1 peptide, expression vector containing a polynucleotide encoding the WT1 peptide, and cells containing the expression vector can be obtained by a technique well known to those skilled in the art. Specifically, the polynucleotide used in the present invention can be determined on the basis of an amino acid sequence of the above WT1 peptide (for example, the amino acid sequence depicted in SEQ ID NO:2). The above polynucleotide can be prepared, for example, by a DNA or RNA synthesis, a PCR method and the like. Also, the types of expression vectors containing the above polynucleotide, sequences contained in addition to the above polynucleotide sequence and the like can be selected properly depending on the purposes, types and the like of hosts into which the expression vectors are introduced. The expression vectors include plasmids, phage vectors, virus vectors and the like. The cells containing an expression vector can be prepared, for example, by transforming host cells. The host cells include *Escherichia coli* cells, yeast cells, insect cells, animal cells and the like. A method for transforming host cells may be a conventional method, and it is possible to use, for example, a calcium phosphate method, a DEAE-dextran method, an electroporation method, and a lipid for gene transfer.

In general, helper T cells are activated when a TCR-CD3 complex on a T cell surface recognizes an antigen peptide through an MHC class II molecule on a surface of antigen presenting cells, and integrin on a T cell surface is stimulated by an integrin ligand on a surface of antigen presenting cells. The activation of helper T cells in the present specification includes not only the activation of helper T cells but also induction and proliferation of helper T cells. Also, helper T cells activated in the present invention may be undifferentiated T cells (for example, naive T cells) and the like. The activated helper T cells have a function that activates an immune system by promoting induction, proliferation and activation of B cells and cytotoxic T cells. Accordingly, the method of the present invention can be used as an adjunctive therapy for treating a cancer and the like. Also, helper T cells activated in vitro using the method of the present invention can be used for treating or preventing a cancer and the like, or as an adjunctive agent therefor. The activation of helper T cells can be evaluated, for example, by measuring the production or secretion of cytokines such as interferons (for example, interferon-γ, etc.) and interleukins.

In another aspect, the present invention provides a composition for activating helper T cells or cytotoxic T cells by adding a WT1 peptide to antigen presenting cells. In the present invention, the activation of cytotoxic T cells may be carried out by passing through the activation of helper T cells. Although a WT1 peptide, a polynucleotide encoding the WT1 peptide, a vector containing the polynucleotide, and cells containing the vector can be exemplified in the composition of the present invention, any molecules may be used providing that they are factors capable of presenting a WT1 peptide as an antigen peptide on a surface of antigen presenting cells. These factors can be obtained by a method well known to those skilled in the art as described above.

The WT1 peptide used in the present invention has the ability to bind to any of an HLA-DRB1*0101 molecule, an HLA-DRB1*0401 molecule, an HLA-DRB1*0403 molecule, an HLA-DRB1*0406 molecule, an HLA-DRB1*0803 molecule, an HLA-DRB1*0901 molecule, an HLA-DRB1*1101 molecule, an HLA-DRB3*0202 molecule, an HLA-DRB4*0101 molecule, an HLA-DRB1*1501 molecule, an HLA-DRB1*0405 molecule, an HLA-DRB1*1502 molecule, an HLA-DPB1*0501 molecule, an HLA-DPB1*0901 molecule, an HLA-DPB1*0201 molecule or an HLA-DPB1*0301 molecule, as described above. Also, the WT1 peptide used in the present invention may have the ability to bind to at least two or more MHC class II molecules of the above MHC class II molecules. Moreover, the WT1 peptide used in the present invention may have the ability to bind to any MHC class II molecule of HLA-DR, HLA-DQ, or HLA-DP molecules.

When the composition of the present invention is administered to a subject having any one or more MHC class II molecules of an HLA-DRB1*0101 molecule, an HLA-DRB1*0401 molecule, an HLA-DRB1*0403 molecule, an HLA-DRB1*0406 molecule, an HLA-DRB1*0803 molecule, an HLA-DRB1*0901 molecule, an HLA-DRB1*1101 molecule, an HLA-DRB3*0202 molecule, an HLA-DRB4*0101 molecule, an HLA-DRB1*1501 molecule, an HLA-DRB1*0405 molecule, an HLA-DRB1*1502 molecule, an HLA-DPB1*0501 molecule, an HLA-DPB1*0901 molecule, an HLA-DPB1*0201 molecule or an HLA-DPB1*0301 molecule, an immune system is activated by activation of helper T cells and/or cytotoxic T cells in the subject. Also, the WT1 gene is highly expressed in various cancers and tumors, for example, in hematological malignancy such as leukemia, myelodysplastic syndrome, multiple myeloma and malignant lymphoma, as well as in solid cancers such as stomach cancer, colorectal cancer, lung cancer, breast cancer, germ-cell cancer, liver cancer, skin cancer, bladder cancer, prostate cancer, uterus cancer, cervical cancer and ovary cancer, and therefore, the composition of the present invention can be used as an adjunctive agent for treating or preventing a cancer. Alternatively, helper T cells, cytotoxic T cells and the like, which are activated using the composition of the present invention, can be used, for example, as an adjunctive agent for treating the above cancers.

In addition to the above WT1 peptide, polynucleotide encoding the WT1 peptide, vector containing the polynucleotide, and cells containing the vector, the composition of the present invention may contain, for example, a carrier, an excipient, an additive and the like. The above WT1 peptide and the like contained in the composition of the present invention activate helper T cells and/or cytotoxic T cells in a WT1 peptide-specific manner, and therefore, the composition may contain a known MHC class I-restrictive WT1 peptide, or may be applied together with such a peptide.

A method for applying the composition of the present invention can be selected properly depending on conditions such as the desired degree of activation of helper T cells and/or cytotoxic T cells, and the state of antigen presenting cells. The application method includes, for example, administration to a subject by intradermal administration, subcutaneous administration, intramuscular administration, intravenous administration, transnasal administration, oral administration and the like, or addition to a culture fluid of antigen presenting cells, but is not limited thereto. The amount of the above WT1 peptide and the like contained in the composition of the present invention, the form of the composition, the application frequency of the composition and the like can be selected properly depending on conditions such as the desired degree of activation of helper T cells and/or cytotoxic T cells, and the state of antigen presenting cells.

In still another aspect, the present invention provides a method for treating or preventing a cancer in a subject, which includes the step of activating helper T cells or cytotoxic T cells by adding a WT1 peptide to antigen presenting cells, wherein the WT1 peptide has the ability to bind to any MHC class II molecule of an HLA-DRB1*0101 molecule, an HLA-DRB1*0401 molecule, an HLA-DRB1*0403 molecule, an HLA-DRB1*0406 molecule, an HLA-DRB1*0803 molecule, an HLA-DRB1*0901 molecule, an HLA-DRB1*1101 molecule, an HLA-DRB3*0202 molecule, an HLA-DRB4*0101 molecule, an HLA-DRB1*1501 molecule, an HLA-DRB1*0405 molecule, an HLA-DRB1*1502 molecule, an HLA-DPB1*0501 molecule, an HLA-DPB1*0901 molecule, an HLA-DPB1*0201 molecule or an HLA-DPB1*0301 molecule. The method of the present invention activates an immune system in a subject by activating helper T cells and/or cytotoxic T cells, thereby treating or preventing a cancer in a subject. In the method of the present invention, the step of activating cytotoxic T cells may be carried out by passing through the step of activating helper T cells. The addition of the WT1 peptide to antigen presenting cells may be carried out directly by addition of the WT1 peptide, or indirectly by addition of a polynucleotide encoding the WT1 peptide or of an expression vector containing a polynucleotide encoding the WT1 peptide or by addition of cells containing the expression vector. The above polynucleotide encoding the WT1 peptide, expression vector containing a polynucleotide encoding the WT1 peptide, and cells containing the expression vector can be obtained by a method well known to those skilled in the art, as described above. Subjects to which the method of the present invention can be applied are those positive in respect to any MHC class II molecule of an HLA-DRB1*0101 molecule, an HLA-DRB1*0401 molecule, an HLA-DRB1*0403 molecule, an HLA-DRB1*0406 molecule, an HLA-DRB1*0803 molecule, an HLA-DRB1*0901 molecule, an HLA-DRB1*1101 molecule, an HLA-DRB3*0202 molecule, an HLA-DRB4*0101 molecule, an HLA-DRB1*1501 molecule, an HLA-DRB1*0405 molecule, an HLA-DRB1*1502 molecule, an HLA-DPB1*0501 molecule, an HLA-DPB1*0901 molecule, an HLA-DPB1*0201 molecule or an HLA-DPB1*0301 molecule. Cancers to which the present invention can be applied may be any cancers, and include, for example, hematopoietic organ tumors such as leukemia, myelodysplastic syndrome, multiple myeloma and malignant lymphoma, as well as solid cancers such as stomach cancer, bowel cancer, lung cancer, breast cancer, germ-cell cancer, liver cancer, skin cancer, bladder cancer, prostate cancer, uterus cancer, cervical cancer and ovary cancer. Also, the method of the present invention may be used together with a method for treating or preventing a cancer using an MHC class I molecule-restrictive WT1 peptide or a pharmaceutical composition therefor.

In still another aspect, the present invention provides use of a WT1 peptide for preparing the above composition, of a polynucleotide encoding the WT1 peptide, of a vector containing the polynucleotide, and of cells containing the vector.

In still further aspect, the present invention relates to a kit containing the above WT1 peptide, polynucleotide encoding the WT1 peptide, vector containing the polynucleotide, or cells containing the vector, for activating helper T cells and/or cytotoxic T cells by adding the WT1 peptide to antigen presenting cells, wherein the WT1 peptide has the ability to bind to any MHC class II molecule of an HLA-DRB1*0101 molecule, an HLA-DRB1*0401 molecule, an HLA-DRB1*0403 molecule, an HLA-DRB1*0406 molecule, an HLA-DRB1*0803 molecule, an HLA-DRB1*0901 molecule, an HLA-DRB1*1101 molecule, an HLA-DRB3*0202 molecule, an HLA-DRB4*0101 molecule, an HLA-DRB1*1501 molecule, an HLA-DRB1*0405 molecule, an HLA-DRB1*1502 molecule, an HLA-DPB1*0501 molecule, an HLA-DPB1*0901 molecule, an HLA-DPB1*0201 molecule or an HLA-DPB1*0301 molecule. Preferably, the kit is used in the above method for activating helper T cells or cytotoxic T cells. The kit of the present invention may contain, for example, an obtaining means of antigen presenting cells, an evaluating means of activity of helper T cells and/or cytotoxic T cells and the like, in addition to the WT1 peptide. In general, the kit is accompanied with an instruction manual. It is possible to effectively activate helper T cells or cytotoxic T cells using the kit of the present invention.

In another aspect, the present invention provides antigen presenting cells which present a complex of an antigen peptide containing a WT1 peptide with an MHC class II molecule. In this case, the MHC class II molecule may be any molecule of an HLA-DRB1*0101 molecule, an HLA-DRB1*0401 molecule, an HLA-DRB1*0403 molecule, an HLA-DRB1*0406 molecule, an HLA-DRB1*0803 molecule, an HLA-DRB1*0901 molecule, an HLA-DRB1*1101 molecule, an HLA-DRB3*0202 molecule, an HLA-DRB4*0101 molecule, an HLA-DRB1*1501 molecule, an HLA-DRB1*0405 molecule, an HLA-DRB1*1502 molecule, an HLA-DPB1*0501 molecule, an HLA-DPB1*0901 molecule, an HLA-DPB1*0201 molecule or an HLA-DPB1*0301 molecule, or may be at least two or more molecules of the above MHC class II molecules. The antigen presenting cells of the present invention may be prepared using a technique known to those skilled in the art. For example, they may be prepared by isolating cells having an antigen presenting ability from a cancer patient, and then pulsing the isolated cells with the above WT1 peptide (for example, peptide having the amino acid sequence as shown in SEQ ID NO:2) or with a polynucleotide encoding the WT1 peptide, or introducing an expression vector containing the polynucleotide into the cells, thereby allowing a complex of an antigen peptide containing the WT1 peptide with an MHC class II molecule to present on the cell surface (Cancer Immunol. Immunother. 46:82, 1998, J. Immunol., 158: p1796, 1997, Cancer Res., 59: p1184, 1999, Cancer Res., 56: p5672, 1996, J. Immunol., 161: p5607, 1998, J. Exp. Med., 184: p465, 1996). In the present specification, the cells having an antigen presenting ability are not limited so far as they express an MHC class II molecule capable of presenting a WT1 peptide on the cell surface, and peripheral blood mononuclear cells or dendritic cells having a high antigen presenting ability are preferred. Also, the presence of the antigen presenting cells of the present invention is confirmed by an increase of activity of cytotoxic T cells, which is confirmed by an increase of an amount of interferon-γ, as shown in the Examples. The antigen presenting cells of the present invention are effectively used in a cell therapy (for example, dendritic cell therapy) as an active ingredient of a pharmaceutical composition.

In still another aspect, the present invention provides helper T cells which recognize a complex of an antigen peptide containing a WT1 peptide with an MHC class II molecule. In this case, the MHC class II molecule may be any molecule of an HLA-DRB1*0101 molecule, an HLA-DRB1*0401 molecule, an HLA-DRB1*0403 molecule, an HLA-DRB1*0406 molecule, an HLA-DRB1*0803 molecule, an HLA-DRB1*0901 molecule, an HLA-DRB1*1101 molecule, an HLA-DRB3*0202 molecule, an HLA-DRB4*0101 molecule, an HLA-DRB1*1501 molecule, an HLA-DRB1*0405 molecule, an HLA-DRB1*1502 molecule, an HLA-DPB1*0501 molecule, an HLA-DPB1*0901 molecule, an HLA-DPB1*0201 molecule or an HLA-DPB1*0301 molecule, or may be at least two or more molecules of the above MHC class II molecules. The helper T cells of the present invention include, for example, those recognizing a complex of an antigen peptide containing a peptide consisting of the amino acid sequence depicted in SEQ ID NO:2 with any MHC class II molecule of an HLA-DRB1*0101 molecule, an HLA-DRB1*0401 molecule, an HLA-DRB1*0403 molecule, an HLA-DRB1*0406 molecule, an HLA-DRB1*0803 molecule, an HLA-DRB1*0901 molecule, an HLA-DRB1*1101 molecule, an HLA-DRB3*0202 molecule, an HLA-DRB4*0101 molecule, an HLA-DRB1*1501 molecule, an HLA-DRB1*0405 molecule, an HLA-DRB1*1502 molecule, an HLA-DPB1*0501 molecule, an HLA-DPB1*0901 molecule, an HLA-DPB1*0201 molecule or an HLA-DPB1*0301 molecule. The helper T cells of the present invention can easily be prepared and obtained by those skilled in the art using a technique known in the art (Iwata, M. et al., Eur. J. Immunol, 26, 2081 (1996)).

In still another aspect, the present invention provides cytotoxic T cells which are activated by helper T cells recognizing a complex of an antigen peptide containing a WT1 peptide with an MHC class II molecule. The cytotoxic T cells of the present invention include, for example, those activated by helper T cells recognizing a complex of an antigen peptide containing a peptide consisting of the amino acid sequence as shown in SEQ ID NO:2 with any MHC class II molecule of an HLA-DRB1*0101 molecule, an HLA-DRB1*0401 molecule, an HLA-DRB1*0403 molecule, an HLA-DRB1*0406 molecule, an HLA-DRB1*0803 molecule, an HLA-DRB1*0901 molecule, an HLA-DRB1*1101 molecule, an HLA-DRB3*0202 molecule, an HLA-DRB4*0101 molecule, an HLA-DRB1*1501 molecule, an HLA-DRB1*0405 molecule, an HLA-DRB1*1502 molecule, an HLA-DPB1*0501 molecule, an HLA-DPB1*0901 molecule, an HLA-DPB1*0201 molecule or an HLA-DPB1*0301 molecule. The cytotoxic T cells of the present invention can easily be prepared by those skilled in the art using a known technique. For example, they are prepared by isolating peripheral blood lymphocytes from a patient, and stimulating them in vitro with a peptide (for example, peptide having the amino acid sequence depicted in SEQ ID NO:2), a polynucleotide encoding the peptide, or an expression vector containing the polynucleotide (Journal of Experimental Medicine 1999, 190:1669). The cytotoxic T cells thus prepared can be used as an active ingredient of a pharmaceutical composition for treating or preventing a cancer and the like. In the Examples of the present specification, an activity to induce cytotoxic T cells was recognized by administration of WT-332 in a sample derived from a subject having a certain MHC class molecule. This shows that antigen presenting cells which present a complex of an antigen peptide consisting of a WT1 peptide with an MHC class II molecule are present in peripheral blood mononuclear cells, and shows the presence of antigen presenting cells which present the complex, helper T cells which specifically recognize them, and cytotoxic T cells induced by the helper T cells.

In still another aspect, the present invention provides an HLA tetramer having the above antigen peptide containing a WT1 peptide and an MHC class II molecule. The MHC class II molecule may be any molecule of an HLA-DRB1*0101 molecule, an HLA-DRB1*0401 molecule, an HLA-DRB1*0403 molecule, an HLA-DRB1*0406 molecule, an HLA-DRB1*0803 molecule, an HLA-DRB1*0901 molecule, an HLA-DRB1*1101 molecule, an HLA-DRB3*0202 molecule, an HLA-DRB4*0101 molecule, an HLA-DRB1*1501 molecule, an HLA-DRB1*0405 molecule, an HLA-DRB1*1502 molecule, an HLA-DPB1*0501 molecule or an HLA-DPB1*0901 molecule, or may be at least two or more molecules of the above MHC class II molecules. In the present specification, the HLA tetramer means a tetramerized product which is obtained by biotinylating a complex (HLA monomer) obtained by association of an HLA protein with a peptide, and then binding the biotinylated product to avidin. HLA tetramers containing various antigen peptides are commercially available, and it is possible to prepare the HLA tetramer of the present invention easily (Science 279: 2103-2106 (1998), Science 274: 94-96 (1996)). The tetramer of the present invention is preferably labeled with fluorescence so that the bound helper T cells and cytotoxic T cells of the present invention can be selected or detected easily by a known detecting means such as flow cytometry and fluorescence microscope. The HLA tetramer in the present invention is not limited to a tetramer, and it is also possible to use a multimer such as a pentamer and a dendrimer, as needed. In the present specification, the multimer means a multimerized product which is obtained by binding two or more complexes (HLA monomers) obtained by association of an HLA protein with a peptide using a known technique.

In another aspect, the present invention provides a pharmaceutical composition for activating helper T cells or cytotoxic T cells, which contains, as an active ingredient, any of the above-mentioned composition, antigen presenting cells, helper T cells, cytotoxic T cells or tetramer. The pharmaceutical composition of the present invention may contain, as an active ingredient, any one or more of the above-mentioned composition, antigen presenting cells, helper T cells, cytotoxic T cells or tetramer. The pharmaceutical composition of the present invention can be used for treating or preventing a cancer. The pharmaceutical composition of the present invention can be applied to various cancers and tumors expressing WT1, for example, to hematopoietic organ tumors such as leukemia, myelodysplastic syndrome, multiple myeloma and malignant lymphoma, as well as to solid cancers such as stomach cancer, bowel cancer, lung cancer, breast cancer, germ-cell cancer, liver cancer, skin cancer, bladder cancer, prostate cancer, uterus cancer, cervical cancer and ovary cancer. Also, the pharmaceutical composition of the present invention can be used for administering to a subject having an MHC class II molecule such as an HLA-DRB1*0101 molecule, an HLA-DRB1*0401 molecule, an HLA-DRB1*0403 molecule, an HLA-DRB1*0406 molecule, an HLA-DRB1*0803 molecule, an HLA-DRB1*0901 molecule, an HLA-DRB1*1101 molecule, an HLA-DRB3*0202 molecule, an HLA-DRB4*0101 molecule, an HLA-DRB1*1501 molecule, an HLA-DRB1*0405 molecule, an HLA-DRB1*1502 molecule, an HLA-DPB1*0501 molecule, an HLA-DPB1*0901 molecule, an HLA-DPB1*0201 molecule or an HLA-DPB1*0301 molecule. The pharmaceutical composition of the present invention may be used together with other method for treating or preventing a cancer or pharmaceutical composition therefor. Moreover, the pharmaceutical composition of the present invention may contain an activating agent, a proliferating agent, an inducing agent and the like of helper T cells or cytotoxic T cells, or may contain a known MHC class I-restrictive WT1 peptide.

In addition to an active ingredient, the pharmaceutical composition of the present invention may contain, for example, a carrier, an excipients and the like. The administration method of the pharmaceutical composition of the present invention can be selected properly depending on conditions such as a type of diseases, a state of subjects and a target site. The method includes, for example, intradermal administration, subcutaneous administration, intramuscular administration, intravenous administration, transnasal administration, oral administration and the like, but is not limited thereto. The amount of the above active ingredient contained in the pharmaceutical composition of the present invention, the dosage form of the composition, the administration frequency of the composition and the like can be selected properly depending on conditions such as a type of diseases, a state of subjects, a target site and the like.

In still another aspect, the present invention provides a method for treating or preventing a cancer, which include the step of administering any of the above-mentioned composition, antigen presenting cells, helper T cells, cytotoxic T cells or tetramer to a subject in an effective amount, wherein the subject has any MHC class II molecule of an HLA- DRB1*0101 molecule, an HLA-DRB1*0401 molecule, an HLA-DRB1*0403 molecule, an HLA-DRB1*0406 molecule, an HLA-DRB1*0803 molecule, an HLA-DRB1*0901 molecule, an HLA-DRB1*1101 molecule, an HLA-DRB3*0202 molecule, an HLA-DRB4*0101 molecule, an HLA-DRB1*1501 molecule, an HLA-DRB1*0405 molecule, an HLA-DRB1*1502 molecule, an HLA-DPB1*0501 molecule, an HLA-DPB1*0901 molecule, an HLA-DPB1*0201 molecule or an HLA-DPB1*0301 molecule. Cancers which can be treated or prevented by the method of the present invention are various cancers and tumors expressing WT1, for example, hematopoietic organ tumors such as leukemia, myelodysplastic syndrome, multiple myeloma and malignant lymphoma, as well as solid cancers such as stomach cancer, bowel cancer, lung cancer, breast cancer, germ-cell cancer, liver cancer, skin cancer, bladder cancer, prostate cancer, uterus cancer, cervical cancer and ovary cancer. The method of the present invention may be used together with other method for treating or preventing a cancer, for example, a method for treating or preventing a cancer using a known MHC class I molecule-restrictive WT1 peptide.

In still another aspect, the present invention provides use of any of the above-mentioned composition, antigen presenting cells, helper T cells, cytotoxic T cells or tetramer for preparing the above pharmaceutical composition.

In one aspect, the present invention relates to an antibody which specifically binds to the above WT1 peptide or polynucleotide encoding the WT1 peptide (hereinafter, the antibody is also referred to as an anti-WT1 antibody). The antibody of the present invention may be either of a polyclonal antibody or a monoclonal antibody. Specifically, an antibody which specifically binds to a peptide having the amino acid sequence as shown in SEQ ID NO:2 and the like may be mentioned. A method for preparing such an antibody is already known, and the antibody of the present invention can be prepared according to such a conventional method as well (Current protocols in Molecular Biology, Ausubel et al. (ed.), 1987, John Wiley and Sons (pub.), Section 11.12-11.13, Antibodies; A Laboratory Manual, Lane, H. D. et al. (ed.), Cold Spring Harbor Laboratory Press (pub.), New York, 1989). For example, a nonhuman animal such as domestic rabbit is immunized using a peptide having the amino acid sequence depicted in SEQ ID NO:2 as an immunogen, and a polyclonal antibody can be obtained from a serum of the animal by a conventional method. On the other hand, in the case of a monoclonal antibody, a nonhuman animal such as mouse is immunized using the peptide used in the present invention (a peptide having the amino acid sequence depicted in SEQ ID NO:2), and the resulting spleen cells and myeloma cells are fused to prepare hybridoma cells, from which the monoclonal antibody can be obtained (Current protocols in Molecular Biology, Ausubel et al. (ed.), 1987, John Wiley and Sons (pub.), Section 11.4-11.11). Also, the preparation of the anti-WT1 antibody of the present invention can be carried out by boosting an immunological reaction using various adjuvants depending on a host. Such adjuvants include a mineral gel (for example, Freund's adjuvant, aluminum hydroxide, etc.), a surfactant, a human adjuvant and the like. The anti-WT1 antibody of the present invention can be used for affinity chromatography, immunological diagnosis and the like. A method for the immunological diagnosis can be selected properly from immunoblotting, radioimmunoassay (RIA), enzyme-linked immunosorbent assay (ELISA), fluorescent or luminescent measurement and the like.

In another aspect, the present invention provides a method for determining the presence or amount of a WT1 peptide in a subject positive in respect to any MHC class II molecule of an HLA-DRB1*0101, HLA-DRB1*0401, HLA-DRB1*0403, HLA-DRB1*0406, HLA-DRB1*0803, HLA-DRB1*0901, HLA-DRB1*1101, HLA-DRB3*0202, HLA-DRB4*0101, or HLA-DRB1*1501 molecule, an HLA-DRB1*0405 molecule, an HLA-DRB1*1502 molecule, an HLA-DPB1*0501 molecule, an HLA-DPB1*0901 molecule, an HLA-DPB1*0201 molecule or an HLA-DPB1*0301 molecule, the method including the steps of:

(a) reacting a sample obtained from the subject with the above anti-WT1 antibody, and then (b) determining the presence or amount of the above anti-WT1 antibody contained in the sample.

A sample obtained from a subject having any MHC class II molecule of an HLA-DRB1*0101, HLA-DRB1*0401, HLA-DRB1*0403, HLA-DRB1*0406, HLA-DRB1*0803, HLA-DRB1*0901, HLA-DRB1*1101, HLA-DRB3*0202, HLA-DRB4*0101, or HLA-DRB1*1501 molecule, an HLA-DRB1*0405 molecule, an HLA-DRB1*1502 molecule, an HLA-DPB1*0501 molecule, an HLA-DPB1*0901 molecule, an HLA-DPB1*0201 molecule or an HLA-DPB1*0301 molecule can be used as a sample used in the above step (a). Samples used in the above step (a) include, for example, body fluid and tissues such as blood and lymphocytes. Those skilled in the art can properly obtain samples, react them with an antibody and carry out other procedures using a known technique. The step (b) in the present invention includes, for example, determination of the localization, site, amount and the like of the above anti-WT1 antibody, and therefore, the present invention can be used for diagnosis, prognosis and the like of a cancer. The above anti-WT1 antibody may be labeled. As a label, known labels such as a fluorescent label and a radioactive label can be used. By labeling, it becomes possible to carry out the determination of the presence or amount of a WT1 peptide simply and rapidly.

In still another aspect, the present invention relates to a kit for determining the presence or amount of a WT1 peptide, which contains the above anti-WT1 antibody as an essential constituent. The kit of the present invention may contain, for example, means for obtaining the anti-WT1 antibody and means for evaluating anti-WT1 antibody, and the like, in addition to the above anti-WT1 antibody. In general, the kit is accompanied with an instruction manual. By using the kit of the present invention, it becomes possible to determine the presence or amount of a WT1 peptide simply and rapidly in the above method for determining the presence or amount of a WT1 peptide.

In still another aspect, the present invention provides a method for determining the presence or amount of WT1-specific helper T cells or WT1-specific cytotoxic T cells in a subject positive in respect to any MHC class II molecule of an HLA-DRB1*0101, HLA-DRB1*0401, HLA-DRB1*0403, HLA-DRB1*0406, HLA-DRB1*0803, HLA-DRB1*0901, HLA-DRB1*1101, HLA-DRB3*0202, HLA-DRB4*0101, or HLA-DRB1*1501 molecule, an HLA-DRB1*0405 molecule, an HLA-DRB1*1502 molecule, an HLA-DPB1*0501 molecule, an HLA-DPB1*0901 molecule, an HLA-DPB1*0201 molecule or an HLA-DPB1*0301 molecule, the method including the steps of:

(a) stimulating a sample obtained from the subject using a WT1 peptide, and (b) determining the presence or amount of cytokines, helper T cells or cytotoxic T cells, and wherein the increase of the presence or amount of cytokines, helper T cells or cytotoxic T cells shows the presence or amount of the WT1-specific helper T cells or WT1-specific cytotoxic T cells.

Samples in the present invention may be any samples so far as they contain antigen presenting cells, and include, for example, peripheral blood mononuclear cells, invasive lymphocytes, tumor cells, cells in ascites fluid, cells in pleural effusion, cells in cerebrospinal fluid, bone marrow cells, lymph node cells and the like. The sample used in the present invention may be derived from healthy donors or from cancer patients. By using those cells derived from healthy donors, for example, it becomes possible to diagnose whether the donors are affected by a cancer, or whether the donors have a predisposition of a cancer, or other conditions. By using those cells derived from cancer patients, for example, it becomes possible to predict whether a WT1 immunotherapy has an effect in the cancer patients, or other conditions. In the method of the present invention, samples obtained may be cultured before and after stimulation with a WT1 peptide, and the culture conditions can be determined properly by those skilled in the art. The stimulation of these cells with a WT1 peptide can be carried out using a known technique such as electroporation, and may be carried out either in vitro or in vivo. The production of a cytokine, the presence of a reaction of helper T cells or cytotoxic T cells, the amount of a cytokine produced, or the amount of helper T cells or cytotoxic T cells reacted can be determined by a known method.

In still another aspect, the present invention relates to a kit for determining the presence or amount of a WT1 peptide, which contains the above WT1 peptide as an essential component. The kit of the present invention may contain, for example, an obtaining means of samples, an evaluating means such as cytokines, in addition to the above WT1 peptide. In general, the kit is attached with an instruction manual. By using the kit of the present invention, it becomes possible to determine the presence or amount of a WT1 peptide simply and rapidly in the above method for determining the presence or amount of a WT1 peptide.

The present invention will be described in detail and specifically by way of examples, but they should not be construed as limiting the present invention.

EXAMPLE 1

1. Induction of WT1-332-Specific Type I Helper T Cells

Peripheral blood mononuclear cells (PBMCs) were separated from peripheral blood of healthy blood donors (donor 1: HLA-DRB1*0406/1201-, DRB3*0101-, and DRB4*0103-positive, donor 2: HLA-DRB1*0901/1101-, DRB3*0202-, and DRB4*0103-positive, donor 3: HLA-DRB1*0401/0405-, and DRB4*0102/0103-positive, donor 4: HLA-DRB1*0901/1101-, DRB3*0202-, and DRB4*0103-positive). The separated PBMCs ($1.5 \times 10^7$ cells) were suspended in a medium composed of 45% RPMI-1640 (SIGMA), 45% AIM-V (Invitrogen), and 10% AB type human serum (MP Biomedicals), and seeded on a 24-well plate at $1.5 \times 10^6$ cells/well (day 0). To the wells seeded with PBMCs, WT1-332 (a peptide consisting of the amino acid sequence depicted in SEQ ID NO:2) was added at a concentration of 10 μg/mL and IL-7 (PeproTech) at a concentration of 10 ng/mL, and the cells were cultured at 37° C. under 5% $CO_2$ for one week. Also, a portion of the separated PBMCs was freeze-preserved for antigen presenting cells in case of re-stimulation.

After one week (on the 7th day), re-stimulation was carried out. First, the freeze-preserved PBMCs were thawed, pulsed with 10 μg/mL WT1-332, treated with 50 μg/mL mitomycin C (Kyowa Hakko Kirin Co., Ltd.), and seeded on a new 24-well plate at $1.0 \times 10^6$ to $1.6 \times 10^6$ cells/well. Next, the cells cultured for one week were recovered, and seeded on wells seeded with antigen presenting cells at $1.0 \times 10^6$ to $1.6 \times 10^6$ cells/well. Finally, IL-7 was added to each well at a concentration of 10 ng/mL, and the cells were cultured at 37° C. under 5% $CO_2$. After 2 days (on the 9th day), a half amount of the culture fluid in each well was gently removed, and instead a medium containing 40 U/mL IL-2 (PeproTech) was added to the well, and the culture was continued. Thereafter, the replacement procedure of a half amount of the culture fluid was carried out every other day using a medium containing 20 U/mL IL-2, and cells were properly recovered between the 14th day and the 21th day and used for experiments.

2. Preparation of Antigen Presenting Cells Used in Experiment for Determination of Restrictive Allele PBMCs were separated from peripheral blood of healthy blood donors (donor 5: HLA-DRB1*0406/1201-, DRB3*0101-, and DRB4*0103-positive, donor 6: HLA-DRB1*0403/1405-, DRB3*0202-, and DRB4*0103-positive, donor 7: HLA-DRB1*0403/1201-, DRB3*0101-, and DRB4*0103-positive, donor 8: HLA-DRB1*0101/0901-, and DRB4*0103-positive, donor 9: HLA-DRB1*1401/1406-, and DRB3*0202-positive, donor 10: HLA-DRB1*0803/0901-, and DRB4*0103-positive, donor 11: HLA-DRB1*1101/1502-, and DRB3*0202-positive, donor 12: HLA-DRB1*0405/1406-, DRB3*0202-, and DRB4*0103-positive, donor 13: HLA-DRB1*0401/0405-, and DRB4*0102/0103-positive, donor 14: HLA-DRB1*0401/1502-, and DRB4*0102-positive, donor 15: HLA-DRB1*0101/0405-, and DRB4*0103-positive, donor 16: HLA-DRB1*0901/1501-, and DRB4*0103-positive, donor 17: HLA-DRB1*0405/1501-, and DRB4*0103-positive, donor 18: HLA-DRB1*1401/1502-, and DRB3*0202-positive, donor 19: HLA-DRB1*1403/1502-, and DRB3*0101-positive, donor 20: HLA-DRB1*0803/1302-, and DRB3*0301-positive), and used as antigen presenting cells used in experiments for determination of a restrictive allele. PBMCs of each donor were freeze-preserved at −80° C. until use.

3. Measurement of IFN-γ (Inhibition of Reaction in the Presence of Anti-HLA-DR Antibody)

T cells induced from PBMCs of donors 1 to 4 were cultured for 24 hours in the absence of WT1-332, in the presence of 10 μg/mL WT1-332, and in the presence of 10 μg/mL WT1-332 and 10 μg/mL anti-HLA-DR antibody (BD Co.). After the culture, the amount of IFN-γ in the supernatant was quantified by ELISA (BD Co.). As a result, it was shown that all the T cells induced recognize WT1-332 and produce IFN-γ, and that the reaction is HLA-DR molecule-restricted.

4. Measurement of IFN-γ (Determination of Restrictive Allele)

T cells induced from PBMCs of donors 1 to 4 were reacted with each of suitable antigen presenting cells pulsed with WT1-332, and a restrictive allele of the T cells induced was determined.

(4-1. T Cells Derived from Donor 1)

T cells induced from PBMCs of donor 1 were co-cultured for 24 hours with antigen presenting cells derived from donors 5, 6, 7, 8 and 9, which were pulsed with 10 μg/mL WT1-332. After the co-culture, the amount of IFN-γ in the supernatant was quantified by ELISA. The results are shown in FIG. 1. T cells derived from donor 1 produced IFN-γ when co-cultured with HLA-DR4 (DRB1*0403, 0406)- positive antigen presenting cells, which revealed that the restrictive allele was HLA-DRB1*0406. Also, it was shown that HLA-DRB1*0403 can present WT1-332 and stimulate T cells.

(4-2. T Cells Derived from Donor 2)

T cells induced from PBMCs of donor 2 were co-cultured for 24 hours with antigen presenting cells derived from donors 10, 11, 12 and 9, which were pulsed with 10 μg/mL WT1-332. After the co-culture, the amount of IFN-γ in the supernatant was quantified by ELISA. The results are shown in FIG. 2. T cells derived from donor 2 produced IFN-γ when co-cultured with HLA-DRB3*0202-positive antigen presenting cells, which revealed that the restrictive allele was HLA-DRB3*0202.

(4-3. T Cells Derived from Donor 3)

T cells induced from PBMCs of donor 3 were co-cultured for 24 hours with antigen presenting cells derived from donors 13, 14, 15 and 10, which were pulsed with 10 μg/mL WT1-332. After the co-culture, the amount of IFN-γ in the supernatant was quantified by ELISA. The results are shown in FIG. 3. T cells derived from donor 3 produced IFN-γ when co-cultured with HLA-DR4 (DRB1*0401, 0405)-positive antigen presenting cells, which revealed that both HLA-DRB1*0401 and 0405 can present WT1-332 and stimulate T cells.

(4-4. T Cells Derived from Donor 4)

T cells induced from PBMCs of donor 4 were co-cultured for 24 hours with antigen presenting cells derived from donors 16, 11, 17, 18, 19 and 20, which were pulsed with 10 μg/mL WT1-332. After the co-culture, the amount of IFN-γ in the supernatant was quantified by ELISA. The results are shown in FIG. 4. T cells derived from donor 4 produced IFN-γ when co-cultured with HLA-DRB1*1101-positive antigen presenting cells, which revealed that the restrictive allele was HLA-DRB1*1101.

EXAMPLE 2

Next, in order to evaluate a binding ability of WT1-332 with MHC class II molecules, a folding test of 7 types of HLA class II monomer proteins (DRB1*1501, 0101, 0405, 0803, 0901, 1502, or DRB4*0101) with WT1-332 was carried out using HPLC. Briefly, a folding reaction solution was prepared by mixing an HLA class II monomer protein, a peptide [a peptide binding to each protein (positive control), a peptide not binding to each protein (negative control), and WT1-332], and a folding buffer. After reacting the solution at 37° C., the retention time was analyzed using HPLC. The folding with WT1-332 was evaluated by utilizing a shift of the retention time due to the binding of an HLA class II monomer protein with a peptide. Reagents used in this test are shown in the following table.

TABLE 1

Reagents used in Test Table 1

| | Supplier |
|---|---|
| SUPERDEX ® 200 | GE Healthcare Sciences |
| Folding buffer | MBL |
| Equilibrating buffer | MBL |
| Positive control peptide: PVSKMRMATPLLMQA (SEQ ID NO: 3) | MBL |
| Negative control peptide: KAERADLLAYLKQATA (SEQ ID NO: 4) | MBL |

Preparation of HLA Class II Monomer Proteins

HLA class II monomer proteins which had been freeze-preserved at −80° C. were thawed on ice. The HLA class II monomer proteins thawed were adjusted using a dilution buffer so that they were contained in an amount of 0.05 mg ($1 \times 10^{-9}$ mol) in 83 μL.

Preparation of Peptide Solutions

About 1 mg of each peptide was weighed by an electronic balance, transferred to a glass vial, and dissolved in DMSO to give a concentration of 20 mg/mL.

Calculation of Amount of Peptide Solution in 50-fold Molar Amount

The amount of a peptide which is a 50-fold molar amount relative to an HLA class II monomer protein was calculated using the following calculation formula.

Amount of peptide required: $1 \times 10^{-9}$ mol$\times 50 = 5 \times 10^{-8}$ mol (amount of peptide required)

$5 \times 10^{-8} \times$(Molecular weight of peptide)$\times 1{,}000=$ (amount of peptide required) (mg)

(Amount of peptide required)/[purity of peptide/100] =(amount of peptide added) (mg)

[(Amount of peptide added)/20 mg/mL]$\times 1{,}000=$ (amount of peptide solution added) (μL)

Calculation of Amount of Folding Buffer Added

As a folding buffer, a 10% amount of a mixed solution of an HLA class II monomer protein and a peptide was added. The amount of the folding buffer added was calculated using the following calculation equation.

[83 μL (Amount of HLA class II monomer protein)+ (amount of peptide solution in 50-fold molar amount)]$\times 0.1=$amount of folding buffer added Analysis of Folding Using HPLC To a glass vial charged with an HLA class II monomer protein, a peptide solution and a folding buffer were added in a calculated amount, and the mixture was allowed to stand at 37° C. overnight. HPLC (Waters 2695 Separation Module) was started, and a SUPERDEX® 200 column was equilibrated with an equilibrating buffer. To all samples, 300 μL of the equilibrate buffer was added and well mixed, and a 100 μL portion of the mixture was used as a sample injection volume to calculate the retention time. Analysis time was 50 minutes. The criterion for the folding of an HLA class II monomer protein with a peptide is a shift of the retention time of not less than 0.1 minute as compared with a control (solvent only). As a result, it was found that the degree of shift of the retention time increased by not less than 0.1 minute in 7 types of HLA class II monomer proteins tested (DRB1*1501, 0101, 0405, 0803, 0901, 1502, or DRB4*0101) (FIG. 5), whereby it became clear that WT1-332 specifically binds to these proteins and can be presented as an antigen.

EXAMPLE 3

Induction of WT1-332-Specific T Cells

Peripheral blood mononuclear cells (PBMCs) were separated from peripheral blood of healthy blood donors (in total 42 donors having at least one of HLA-DRB1*501, 1502, 0405, HLA-DPB1*0501, and 0901). The separated PBMCs were divided into portions of $1.2 \times 10^7$ cells, suspended in a medium composed of 45% RPMI-1640 (SIGMA), 45% AIM-V (Invitrogen), and 10% AB type human serum (MP Biomedicals), and seeded on a 24-well plate at $1.5 \times 10^6$ cells/well (on the 0th day). To the wells seeded with PBMCs, WT1-332 was added at a concentration of 20 μg/mL and IL-7 (PeproTech) at a concentration of 10 ng/mL, and the cells were cultured at 37° C. under 5% $CO_2$ for one week. A group in which a solvent (10 mM acetic acid) was added instead of WT1-332 at a final concentration of 10 μM (solvent induction group) was set as a control group. Also, a portion of the separated PBMCs was freeze-preserved for antigen presenting cells when re-stimulating.

After one week (on the 7th day), re-stimulation was carried out. First, the freeze-preserved PBMCs were thawed, pulsed with 20 μg/mL WT1-332 or 10 μM acetic acid solvent, treated with 50 μg/mL mitomycin C (Kyowa Hakko Kirin Co., Ltd.), and seeded on a new 24-well plate at $1.0 \times 10^6$ to $1.6 \times 10^6$ cells/well. Next, the cells cultured for one week were recovered, and seeded on wells seeded with antigen presenting cells at $1.0 \times 10^6$ to $1.6 \times 10^6$ cells/well. Finally, IL-7 was added to each well at a concentration of 10 ng/mL, and the cells were cultured at 37° C. under 5% $CO_2$. After 2 days (on the 9th day), a half amount of the culture fluid in each well was gently removed, and instead a medium containing 40 U/mL IL-2 (PeproTech) was added to the well, and the culture was continued. Thereafter, the replacement procedure of a half amount of the culture fluid was carried out every other day using a medium containing 20 U/mL IL-2.

Cells were recovered on the 0th day, 7th day, and 14th day, and used in experiments for measurement of IFN-γ.
Measurement of IFN-γ [Intracellular Cytokine Staining (ICS)]

Antigen re-stimulation was carried out by seeding PBMCs on the 0th day after preparation and living cells recovered on day 7 and day 14 from a WT1-332 induction group and a solvent induction group on a 96-well U-bottom plate, and adding a WT1-332 containing medium at a final concentration of 20 μg/mL. Also, a solvent containing medium was added at a final concentration of 10 μM as a control. After culturing the cells at 37° C. under 5% $CO_2$ for 4 hours, Brefeldin A (BioLegend) was added and the culture was further continued. After 6 hours from the start of culture, cells were recovered and stained with a PE-labeled anti-human CD4 antibody and an FITC-labeled anti-human CD8 antibody. Intracellular IFN-γ staining was carried out using BD Cytofix/Cytoperm Fixation/Permiabilization Kit (Becton Dickinson) and a PerCP/Cy5.5-labeled anti-human IFN-γ antibody. EPICS-XL MCL (Beckman Coulter) was used for analysis. The results are shown in FIGS. 6 and 7. From FIG. 6, it was confirmed that, in the WT1-332 induction group, the WT1-332-specific Th1 remarkably and time-dependently increased between the 7th day and the 14th day. The increase was significant relative to the solvent induction group ($P<0.0001$). From FIG. 7, it was confirmed that, in the WT1-332 induction group, the WT1-332-specific CTL time-dependently increased between the 7th day and the 14th day, and the increase was significant relative to the solvent induction group ($P<0.0001$).
Measurement of IFN-γ (Inhibition of Reaction in the Presence of Anti-HLA-DR Antibody and Anti-HLA-DQ Antibody)

On the 14th day, T cells induced from PBMCs of donors 21 to 37 were cultured for 24 hours in the presence of 10 μM of a solvent, in the presence of 20 μg/mL of WT1-332, and in the presence of 20 μg/mL of WT1-332 and 10 μg/mL of an anti-HLA-DR antibody (L243[G46-6], BD Co.). After the culture, the amount of IFN-γ in the supernatant was quantified by ELISA (BD Co.). The results are shown in FIG. 8. In samples from donors 21 to 37, it was shown that the T cells induced recognize WT1-332 and produce IFN-γ, and that the reaction is HLA-DR molecule-restricted.

Also, on the 14th day, T cells induced from PBMCs of donors 38 to 46 were cultured for 24 hours in the presence of 10 μM of a solvent, in the presence of 20 μg/mL of WT1-332, and in the presence of 20 μg/mL of WT1-332 and 10 μg/mL of an anti-HLA-DR antibody (L243[G46-6], BD Co.) or 10 μg/mL of an anti-HLA-DQ antibody (SPVL3, BC Co.). After the culture, the amount of IFN-γ in the supernatant was quantified by ELISA (BD Co.). The results are shown in FIG. 11. In samples from donors 38 to 46, the T cells induced recognized WT1-332 and produced IFN-γ, and the reaction was not inhibited by the anti-HLA-DR antibody and the anti-HLA-DQ antibody. As is apparent from these facts, the WT1-332-induced T cells derived from donors 38 to 46 are HLA-DP molecule-restricted.
Induction of WT1-332-Specific T Cells (Relationship with New Allele)

With respect to each of 17 samples (donors 21 to 37) which were HLA-DR-restricted and had WT1-332-specific Th1 induced, in the results using healthy blood donors (in total 42 donors having at least one of HLA-DRB1*1501, 1502, 0405, HLA-DPB1*0501, and 0901) in FIGS. 6 and 7, the result on the 14th day is shown in FIGS. 9 and 10. Also, the HLA class II type (type of HLA-DRB1 allele and HLA-DPB1 allele) of each of 17 samples (donors 21 to 37) is shown in the following Table 2. In this connection, DRB3*0202 is in linkage disequilibrium with DRB1*1101, DRB1*1401 and DRB1*1405 (DRB1 allele denoted by the symbol "Δ" in the table), and DRB4*0101 is in linkage disequilibrium with DRB1*0403, DRB1*0405 and DRB1*0901 (DRB1 allele denoted by the symbol "▲" in the Table). In the Table, alleles denoted by a bold, italic letter represent a new compatible HLA-DRB1 allele.

TABLE 2

| Donor No. | HLA class II type | | | |
|---|---|---|---|---|
| | DRB1 allele | | DPB1 allele | |
| 21 | *0901* ▲ | 1401Δ | 0501 | 0501 |
| 22 | *0101* | *0901* ▲ | 0402 | 0501 |
| 23 | *0401* | 0405▲ | 0501 | 0501 |
| 24 | *0406* ▲ | 1501 | 0201 | 0501 |
| 25 | 1401Δ | 1502 | 0201 | 0901 |
| 26 | *0901* ▲ | *1101*Δ | 0501 | 0501 |
| 27 | *1101*Δ | 1502 | 0401 | 0901 |
| 28 | *0803* | *0901* ▲ | 0201 | 0501 |
| 29 | 1401Δ | 1502 | 0501 | 0901 |
| 30 | 0405▲ | 1501 | 0501 | 0501 |
| 31 | 0405▲ | 1405Δ | 0501 | 0501 |
| 32 | *0403* ▲ | 1501 | 0402 | 0501 |
| 33 | *0101* | 0405▲ | 0402 | 0501 |
| 34 | 1403 | 1501 | 0201 | 0501 |
| 35 | 1202 | 1501 | 0201 | 0501 |
| 36 | 0405▲ | *0406* ▲ | 0201 | 0501 |
| 37 | *0101* | 1501 | 0402 | 0501 |

From FIG. 9, FIG. 10 and Table 2, induction of WT1-332-specific Th1 and WT1-332-specific CTL was recognized in cells having these HLA-DR alleles.

Also, with respect to each of 9 samples (donors 38 to 46) which were HLA-DP-restrictive and had WT1-332-specific Th1 induced, in the results using healthy blood donors (in total 42 donors having at least one of HLA-DRB1*1501, 1502, 0405, HLA-DPB1*0501, and 0901) in FIGS. 6 and 7, the result on the 14th day is shown in FIGS. 12 and 13. Also, the HLA class II type (type of HLA-DRB1 allele and HLA-DPB1 allele) of each of 9 samples (donors 38 to 46) is shown in the following Table 3. In the table, the symbol "*" denotes compatible HLA-DPB1 alleles previously known.

TABLE 3

| Donor No. | HLA class II type | | | |
|---|---|---|---|---|
| | DRB1 allele | | DPB1 allele | |
| 38 | 0901 | 1401 | 0501* | 0501* |
| 39 | 1201 | 1201 | 0201 | 0501* |
| 40 | 1502 | 1502 | 0901* | 0901* |
| 41 | 0401 | 1502 | 0201 | 0901* |
| 42 | 1501 | 1502 | 0201 | 0901* |
| 43 | 0405 | 0901 | 0201 | 0301 |
| 44 | 1501 | 1502 | 0501* | 0901* |
| 45 | 0405 | 1406 | 0201 | 0501* |
| 46 | 1302 | 1502 | 0201 | 0901* |

From FIG. 12, FIG. 13 and Table 3, induction of WT1-332-specific Th1 and WT1-332-specific CTL was recognized in cells having these HLA-DP alleles.

INDUSTRIAL APPLICABILITY

The present invention provides a method for activating helper T cells and/or cytotoxic T cells using a WT1 peptide having the ability to bind to any MHC class II molecule of an HLA-DRB1*0101 molecule, an HLA-DRB1*0401 molecule, an HLA-DRB1*0403 molecule, an HLA-DRB1*0406 molecule, an HLA-DRB1*0803 molecule, an HLA-DRB1*0901 molecule, an HLA-DRB1*1101 molecule, an HLA-DRB3*0202 molecule, an HLA-DRB4*0101 molecule, an HLA-DRB1*1501 molecule, an HLA-DRB1*0405 molecule, an HLA-DRB1*1502 molecule, an HLA-DPB1*0501 molecule, an HLA-DPB1*0901 molecule, an HLA-DPB1*0201 molecule or an HLA-DPB1*0301 molecule and a composition therefor, a pharmaceutical composition for treating and/or preventing a cancer by activating helper T cells and/or cytotoxic T cells, and the like. Thus, the present invention is applicable to the field of pharmaceuticals and the like, for example, development and production fields of preventives or remedies for various hematopoietic organ tumors and solid cancer highly expressing a WT1 gene.

The invention claimed is:

1. A method for producing an activated helper T cell, comprising:
   contacting a WT1 peptide with an antigen-presenting cell comprising one or two MHC class II molecules selected from the group consisting of an HLA-DRB1*0403 molecule, an HLA-DRB1*0406 molecule, an HLA-DRB1*0803 molecule, an HLA-DRB3*0202 molecule, an HLA-DRB4*0101 molecule, an HLA-DPB1*0201 molecule, and an HLA-DPB1*0301 molecule,
   wherein the WT1 peptide consists of the amino acid sequence of SEQ ID NO: 2 and is capable of binding to the one or two MHC class II molecules.

2. The method of claim 1, wherein the antigen-presenting cell comprises two of the MHC class II molecules.

3. The method of claim 1, wherein the antigen-presenting cell further comprises an HLA-DRB1*0405 molecule, an HLA-DRB1*1501 molecule, an HLA-DRB1*1502 molecule, an HLA-DPB1*0501 molecule, an HLA-DPB1*0901 molecule, or a combination thereof, to which the WT1 peptide is capable of binding.

4. The method of claim 1, wherein the WT1 peptide is modified by esterification, alkylation, halogenation, or phosphorylation of a functional group in a side chain of an amino acid residue of the WT1 peptide, or addition of a histidine tag or a detectable label to the WT1 peptide.

5. The method of claim 1, wherein the antigen-presenting cell is an isolated dendritic cell.

6. The method of claim 1, wherein the antigen-presenting cell is an isolated peripheral blood mononuclear cell.

7. A method for producing an activated helper T cell, comprising:
   contacting a WT1 peptide with an antigen-presenting cell comprising at least one of an isolated dendritic cell and an isolated peripheral blood mononuclear cell, and comprising one or two MHC class II molecules selected from the group consisting of an HLA-DRB1*0403 molecule, an HLA-DRB1*0406 molecule, an HLA-DRB1*0803 molecule, an HLA-DRB3*0202 molecule, an HLA-DRB4*0101 molecule, an HLA-DPB1*0201 molecule, and an HLA-DPB1*0301 molecule,
   wherein the WT1 peptide consists of the amino acid sequence of SEQ ID NO: 2 and is capable of binding to the one or two MHC class II molecules.

8. The method of claim 7, wherein the antigen-presenting cell is an isolated dendritic cell.

9. The method of claim 7, wherein the antigen-presenting cell is an isolated peripheral blood mononuclear cell.

10. A method for producing an activated helper T cell in vivo, comprising:
    administering a WT1 peptide to a subject having an antigen-presenting cell such that the WT1 peptide is contacted with the antigen-presenting cell in vivo, wherein the antigen-presenting cell comprises one or two MHC class II molecules selected from the group consisting of an HLA-DRB1*0403 molecule, an HLA-DRB1*0406 molecule, an HLA-DRB1*0803 molecule, an HLA-DRB3*0202 molecule, an HLA-DRB4*0101 molecule, an HLA-DPB1*0201 molecule, and an HLA-DPB1*0301 molecule, and
    the WT1 peptide consists of the amino acid sequence of SEQ ID NO: 2 and is capable of binding to the one or two MHC class II molecules.

11. The method of claim 1, wherein the activated helper T cell is produced in vitro.

12. A method for activating a helper T cell in a subject requiring the activation, comprising:
    administering a WT1 peptide to the subject who has one or two MHC class II molecules selected from the group consisting of an HLA-DRB1*0101 molecule, an HLA-DRB1*0401 molecule, an HLA-DRB1*0403 molecule, an HLA-DRB1*0406 molecule, an HLA-DRB1*0803 molecule, an HLA-DRB1*0901 molecule, an HLA-DRB1*1101 molecule, an HLA-DRB3*0202 molecule, an HLA-DRB4*0101 molecule, an HLA-DPB1*0201 molecule, and an HLA-DPB1*0301 molecule,
    wherein the WT1 peptide is capable of binding to the one or two MHC class II molecules, and consists of the amino acid sequence of SEQ ID NO: 2, and
    the subject has cancer cells endogenously expressing the Wilms' tumor 1 gene (WT1).

13. A method, comprising:
    administering a WT1 peptide to a subject who has been diagnosed with cancer and has an MHC class II molecule selected from the group consisting of an HLA-DRB1*0101 molecule, an HLA-DRB1*0401 molecule, an HLA-DRB1*0403 molecule, an HLA-DRB1*0406 molecule, an HLA-DRB1*0803 molecule, an HLA-DRB1*0901 molecule, an HLA-DRB1*1101 molecule, an HLA-DRB3*0202 molecule, an HLA-DRB4*0101 molecule, an HLA-DPB1*0201 molecule, and an HLA-DPB1*0301 molecule,
    wherein the WT1 peptide consists of the amino acid sequence of SEQ ID NO: 2 and is capable of binding to the MHC class II molecule, and
    the cancer cells endogenously express the Wilms' tumor 1 gene (WT1).

14. The method of claim 1, wherein the antigen-presenting cell comprises one of the MHC class II molecules.

15. The method of claim 3, wherein the WT1 peptide is modified by esterification, alkylation, halogenation, or phosphorylation of a functional group in a side chain of an amino acid residue of the WT1 peptide, or addition of a histidine tag or a detectable label to the WT1 peptide.

16. The method of claim 3, wherein the antigen-presenting cell is an isolated dendritic cell.

17. The method of claim 3, wherein the antigen-presenting cell is an isolated peripheral blood mononuclear cell.

18. The method of claim 3, wherein the activated helper T cell is produced in vitro.

19. The method of claim 15, wherein the antigen-presenting cell is an isolated dendritic cell.

20. The method of claim 15, wherein the antigen-presenting cell is an isolated peripheral blood mononuclear cell.

* * * * *